United States Patent
Bhattacharya et al.

(10) Patent No.: US 8,766,633 B2
(45) Date of Patent: Jul. 1, 2014

(54) METHODS AND APPARATUS FOR PASADENA HYPERPOLARIZATION

(75) Inventors: Pratip Bhattacharya, Pasadena, CA (US); Brian D. Ross, Altadena, CA (US)

(73) Assignee: Huntington Medical Research Institutes, Pasadena, CA (US)

( * ) Notice: Subject to any disclaimer, the term of this patent is extended or adjusted under 35 U.S.C. 154(b) by 800 days.

(21) Appl. No.: 12/904,941

(22) Filed: Oct. 14, 2010

(65) Prior Publication Data

US 2011/0095759 A1    Apr. 28, 2011

Related U.S. Application Data

(63) Continuation-in-part of application No. PCT/US2009/040568, filed on Apr. 14, 2009.

(60) Provisional application No. 61/044,615, filed on Apr. 14, 2008.

(51) Int. Cl.
    *G01V 3/00*      (2006.01)

(52) U.S. Cl.
    USPC .......................................... 324/309; 324/307

(58) Field of Classification Search
    USPC ................... 324/309, 307, 306, 300
    See application file for complete search history.

(56) References Cited

U.S. PATENT DOCUMENTS

| | | | |
|---|---|---|---|
| 5,492,814 A | 2/1996 | Weissleder | |
| 5,642,625 A * | 7/1997 | Cates et al. | 62/55.5 |
| 5,726,571 A | 3/1998 | Guclu et al. | |
| 5,965,133 A | 10/1999 | Cantor et al. | |
| 6,008,644 A | 12/1999 | Leunbach et al. | |
| 6,108,574 A | 8/2000 | Ardenkjaer-Larsen et al. | |
| 6,278,893 B1 | 8/2001 | Ardenkjaer-Larsen et al. | |
| 6,311,086 B1 | 10/2001 | Ardenkjaer-Larsen et al. | |
| 6,453,188 B1 | 9/2002 | Ardenkjaer-Larsen et al. | |
| 6,466,814 B1 | 10/2002 | Ardenkjaer-Larsen et al. | |
| 6,574,495 B1 | 6/2003 | Golman et al. | |
| 6,574,496 B1 | 6/2003 | Golman et al. | |

(Continued)

FOREIGN PATENT DOCUMENTS

| | | |
|---|---|---|
| WO | WO2004/019996 A1 | 3/2004 |
| WO | WO2004/019997 A1 | 3/2004 |

(Continued)

OTHER PUBLICATIONS

International PCT Search Report and Written Opinion dated Jan. 18, 2008 for PCT/US06/39974.

(Continued)

*Primary Examiner* — Louis Arana

(74) *Attorney, Agent, or Firm* — Davis Wright Tremaine LLP

(57) ABSTRACT

The present subject matter relates to methods and apparatus for using hyperpolarization to improve imaging. Am exemplary embodiment, a PASADENA polarizer, is capable of delivering 2.5-5 ml of highly hyperpolarized biological $^{13}C$ and $^{15}N$ imaging reagents in less than one minute, and capable of repeated delivery every 5-8 minutes. Exemplary quality control sequences are also provided to create versatile methods, systems, and apparatuses for a variety of biomolecules, capable of undergoing reaction with parahydrogen necessary for effective PASADENA. The subject matter simplifies the technology for routine liquid state generation of hyperpolarized molecules for $^{13}C$ and $^{15}N$ subsecond imaging and spectroscopy in vivo and further advance the clinical application of this technology. Methods and systems for providing magnetic shielding are also provided.

12 Claims, 21 Drawing Sheets

(56) References Cited

U.S. PATENT DOCUMENTS

| | | | |
|---|---|---|---|
| 6,711,440 | B2 | 3/2004 | Deal et al. |
| 6,727,697 | B2 | 4/2004 | Fiat |
| 6,872,380 | B2 | 3/2005 | Axelsson et al. |
| 7,256,047 | B2 | 8/2007 | Malloy et al. |
| 7,501,236 | B1 * | 3/2009 | Knox et al. ................. 435/6.11 |
| 2002/0137965 | A1 | 9/2002 | Axelsson et al. |
| 2003/0124732 | A1 | 7/2003 | Axelsson et al. |
| 2003/0157020 | A1 | 8/2003 | Petersson et al. |
| 2003/0212323 | A1 | 11/2003 | Petersson et al. |
| 2004/0024307 | A1 | 2/2004 | Golman et al. |
| 2006/0104906 | A1 * | 5/2006 | Ardenkjaer-Larsen et al. ............................. 424/9.3 |
| 2006/0127313 | A1 | 6/2006 | Goldman et al. |
| 2006/0173283 | A1 | 8/2006 | Axelsson et al. |
| 2007/0025918 | A1 | 2/2007 | Hurd |
| 2007/0140966 | A1 | 6/2007 | Chang et al. |
| 2009/0264732 | A1 | 10/2009 | Ross et al. |
| 2010/0092391 | A1 | 4/2010 | Ross |
| 2010/0233089 | A1 | 9/2010 | Ross et al. |

FOREIGN PATENT DOCUMENTS

| | | | |
|---|---|---|---|
| WO | WO2004/090563 | A1 | 10/2004 |
| WO | WO2006/011809 | A1 | 2/2006 |
| WO | WO2006/011810 | A3 | 2/2006 |
| WO | WO2006/011811 | A3 | 2/2006 |
| WO | WO2006/054903 | A3 | 5/2006 |
| WO | WO2007/044867 | A3 | 4/2007 |
| WO | WO2008/086534 | A1 | 7/2008 |
| WO | WO2009/046457 | A3 | 4/2009 |
| WO | WO2009/129265 | A1 | 10/2009 |

OTHER PUBLICATIONS

International Preliminary Report on Patentability issued Apr. 7, 2009 for PCT/US06/39974.
International PCT Search Report and Written Opinion dated May 20, 2008 for PCT/US08/50932.
International Preliminary Report on Patentability issued Jul. 14, 2009 for for PCT/US08/50932.
International PCT Search Report and Written Opinion dated Aug. 18, 2009 for PCT/US08/78999.
International Preliminary Report on Patentability issued Apr. 7, 2010 for PCT/US08/78999.
International PCT Search Report and Written Opinion dated Jun. 9, 2009 for PCT/US09/40568.
International PCT International Preliminary Report on Patentability dated Oct. 28, 2010 for PCT/US09/40568.
Albert, M.S. et al., Biological Magnetic-Resonance-Imaging Using Laser Polarized 129 XE, Nature, 1994, 370:199-201.
Ardenkjaer-Larsen, J.H. et al., Increase in signal-to-noise ratio of > 10,000 times in liquid-state NMR, Proc. Natl. Acad. Sci. USA, 100(18):10158-63 (2003).
Bargon et al., Parahydrogen induced polarization, Progress in nuclear magnetic resonance spectroscopy 31, 1997, Part 4:293-315.
Bhattacharya, P. et al., Towards hyperpolarized 13C-succinate imaging of brain cancer, J Magn Reson, 2007, 186:108-113.
Bhattacharya, P. et al., Ultra fast three dimensional imaging of Hyperpolarized 13C In Vivo. MAGMA, 18.5, 245-256 (2005).
Bowers, C.R. and Weitekamp, D.P., Parahydrogen and Synthesis Allow Dramatically Enhanced Nuclear Alignment, J. Am. Chem. Soc., 109:5541-5542 (1987).
Bowers, C.R. and Weitekamp, D.P., Transformation of symmetrization order to nuclear-spin magnetization by chemical reaction and nuclear magnetic resonance, Phys. Rev. Lett., 57(21):2645-2648 (1986).
Chekmenev, E.Y. et al., Pasadena Hyperpolarization of Succinic Acid for MRI and NMR Spectroscopy, Journal of the American Chemical Society, 2008, 130:pp. 1-7.
Esteban, M.A. et al., HIF, a missing link between metabolism and cancer, Nature Medicine, 2005, 11:1047-1048.
Fayad, Z.A. et al., Serial, noninvasive, in vivo magnetic resonance microscopy detects the development of atherosclerosis in apolipoprotein E-deficient mice and its progression by arterial wall remodeling, J. Magn. Reson. Imag., 17(2):184-189 (2003).
Forsen S. et al., S. and Hoffman, R.A., Study of moderately rapid chemical exchange reactions by means of nuclear magnetic double resonance, J. Chem. Phys., 39: 2892-2901 (1963).
Golman, K. et al., Molecular imaging with endogenous substances, PNAS, vol. 100, No. 18, pp. 10435-01439 (Sep. 2, 2003).
Golman, K. et al., Molecular imaging using hyperpolarized 13C, British J. of Radiol., 76: S118-S127 (2003).
Golman, K. et al., Parahydrogen-Induced Polarization in Imaging: Subsecond 13C Angiography, Magnetic Resonance in Medicine, 46:1-5 (2001) pp. 1-5.
Goldman, M. et al., Conversion of a proton pair para order into 13C polarization by r. f. irradiation, for use in MRI, Comptes Rendus Physique, 2005, 6:575-581.
Goldman, M. et al., Design and implementation of 13C hyperpolarization from para-hydrogen, for new MRI contrast agents, Comptes Rendus Chimie, 2008, 9:357-363.
Goldman, M. et al., Hyperpolarization of 13C through order transfer from parahydrogen: A new contrast agent for MRI, Magnetic Resonance Imaging, 2005, 23:153-157.
Johannesson, H. et al., Transfer of para-hydrogen spin order into polarization by diabatic field cycling, C. R. Physique, 5:315-324 (2004).
Kuhn, L. et al., Transfer of parahydrogen-induced hyperpolarization to heteronuclei, Top Curr Chem, 2007, 276:25-68.
Mansson, S. et al., 13C imaging—a new diagnostic platform, European Radiology, 2006, 16:57-67.
Rustin, P. et al., Succinate dehydrogenase and human diseases: new insights into a well-known enzyme, European Journal of Human Genetics, 2002, 10:289-291.
Schmued, L.C. et al., Intracranial injection of Fluoro-Gold results in the degeneration of local but not retrogradely labeled neurons, Brain Res., 626(1-2):71-77 (1993).
Smith, S.A. et al., Computer-Simulations in Magnetic-Resonance—an Object-Oriented Programming Approach, Journal of Magnetic Resonance Series A, 1994, 106:75-105.
Snapper, I. et al., Pharmacology and therapeutic value of diamidine derivatives, particularly of 2-hydroxystilbamidine, Trans. NY Acad. Sci., 14(7):269-271 (1952).
Tam, S. et al., Ortho/para hydrogen converter for rapid deposition matrix isolation spectroscopy, Review of Scientific Instruments, 1999, 70:1926-1932.
European Publication No. EP1933884 (Huntington Medical Research Institute), corresponds to WO 2007/044867, bibliographic data attached.
European Publication No. EP2117607 (Huntington Medical Research Institute), corresponds to WO 2008/086534, bibliographic data attached.

* cited by examiner

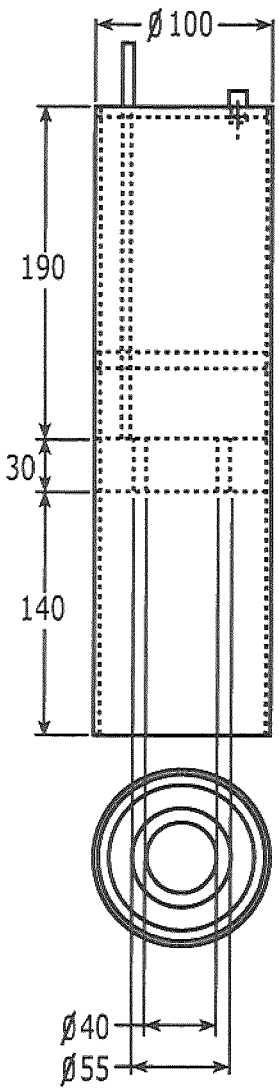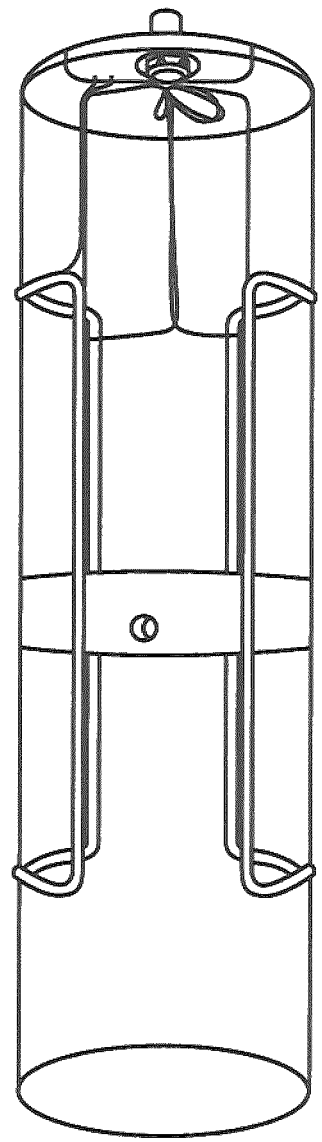
FIG. 3a
FIG. 3b $^{13}C$ Chemical Shift (ppm)

$^{1}H$ Chemical Shift (ppm)

METHODS AND APPARATUS FOR PASADENA HYPERPOLARIZATION

CROSS-REFERENCE TO RELATED APPLICATIONS

This application is a continuation-in-part of International Application No. PCT/US2009/040568 filed on Apr. 14, 2009, which in turn claims the benefit of U.S. Provisional Application No. 61/044,615 filed on Apr. 14, 2008, each of which are hereby incorporated by reference herein in their entirety.

FIELD OF THE SUBJECT MATTER

The field of the subject matter relates to methods and apparatus for imaging biological subjects by magnetic resonance imaging. More specifically, the present subject matter teaches methods and apparatus utilizing hyperpolarization to deliver biological imaging reagents for biological imaging. The present subject matter further teaches methods and systems for shielding the hyperpolarization system from stray magnetic fields.

BACKGROUND OF THE SUBJECT MATTER

All publications cited herein are incorporated by reference to the same extent as if each individual publication or patent application was specifically and individually indicated to be incorporated by reference. The following description includes information that may be useful in understanding the present subject matter. It is not an admission that any of the information provided herein is prior art or relevant to the presently claimed subject matter, or that any publication specifically or implicitly referenced is prior art.

Magnetic resonance imaging ("MRI") is a commonly-accepted technique used in medical imaging to visualize the structure and function of the body and provide detailed images in any plane. In MRI, a scanner creates a powerful magnetic field which aligns the magnetization of hydrogen atoms in a biological subject. Radio waves are used to alter the alignment of this magnetization, causing the hydrogen atoms to emit a weak radio signal which is amplified by the scanner. This technology is useful in connection with disease diagnosis and prognosis, and in the broader study of biological systems. Indeed, many hospitals and medical facilities have MRI imaging equipment on-site, and routinely make use of it to aid in the diagnosis and monitoring of an array of diseases and physiologic conditions. However, as MRI technology has progressed very little there remains a strong need in the art for improvements in MRI methods and apparatus, specifically improvements in image quality and reproducibility.

Several promising methods of improving nuclear magnetic resonance ("NMR") signal, including high field, rapid gradients, parallel radio frequency (R.F. or r.f.) excitation and acquisition, super-cooled R.F.-coils, rapid imaging and magnetization transfer sequences, as well as paramagnetic contrast agents, have been proposed and researched. However, these methods all operate within the constraints of Boltzman distribution and therefore can only provide incremental improvements in the signal to noise ratio ("SNR") in MRI, varying from 2-10 fold [J. H. Gillard, A. D. Waldman, and P. B. Barker, *Clinical MR Neuroimaging: Diffusion, Perfusion and Spectroscopy*, Cambridge University Press, New York, N.Y., 2005].

However, a family of hyperpolarization techniques exist which address the issue of low SNR by developing polarization several orders of magnitude greater than that predicted in the Boltzman equation, and by using a variety of physical and chemical methods to approach polarization of unity (P=100%). Hyperpolarized noble gas imaging has been practiced by scientists and clinicians for over ten years with great success. The use of xenon gas has been in use by clinicians for two or more years [M. S. Albert, G. D. Cates, B. Driehuys, W. Happer, B. Saam, C. S. Springer, and A. Wishnia, *Biological Magnetic-Resonance-Imaging Using Laser Polarized Xe-129*. Nature 370 (1994) 199-201]. Hyperpolarized heteronuclear NMR with $^{13}C$ and $^{15}N$ became available for in vivo applications through the systematic improvement and exploitation of dynamic nuclear polarization ("DNP") [J. H. Ardenkjaer-Larsen et al., *Increase in signal-to-noise ratio of >10,000 times in liquid-state NMR*. Proceedings of the National Academy of Sciences of the United States of America 100 (2003) 10158-10163] and parahydrogen-induced polarization ("PHIP") [C. R. Bowers, and D. P. Weitekamp, *Para-Hydrogen and Synthesis Allow Dramatically Enhanced Nuclear Alignment*. Journal of the American Chemical Society 109 (1987) 5541-5542]. U.S. Pat. No. 6,574,495 to Golman et al., and U.S. Pat. No. 6,872,380 to Axelsson et al., describe apparatus and processes for using PHIP, which is also known as PASADENA (parahydrogen and synthesis allow dramatically enhanced nuclear alignment).

Although PASADENA provides much needed improvement in MRI technology, PASADENA is only utilized in a few laboratories. Cost factors combined with the operational complexity of current PASADENA apparatus have proven problematic in advancing the technique, which has lead to secondary disadvantages including lack of multi-site comparisons and limiting studies to improve on and examine the merits of PASADENA, handicapping further development and propagation of the technique. Commercial devices based on DNP are available; however, the efficiency of such machines is less than ideal. For example, it takes as long as 90 minutes to complete a cycle using a DNP-based device.

The present subject matter is written to overcome this barrier by describing construction of a simple PASADENA polarizer which will provide low-cost access to PASADENA hyperpolarization, allow a systematic comparison between DNP and PASADENA and encourage avenues which appear to offer great promise for in vivo hyperpolarized MRI studies not readily amenable to DNP or hyperpolarized noble gases. In addition, the subject matter describes methods for installing, calibrating and operating the polarizer to optimize PASADENA hyperpolarization. While the ground breaking early discoveries, and some of the subsequent advancements in PASADENA method [Kuhn L. T., Bargon J., *Transfer of parahydrogen-induced hyperpolarization to heteronuclei*. Top Curr Chem 276: (2007) 25-68] required only an NMR spectrometer, an unsaturated molecule and a supply of parahydrogen gas, levels of hyperpolarization reported were generally around 1%, which are insufficient for biological, pre-clinical or clinical studies. Accordingly, a polarizer interface is needed to allow for rapid mixing and chemical reaction of parahydrogen, $^{13}C$ (or $^{15}N$) enriched precursor in a catalyst solution under the correct conditions, within a low field NMR unit. The high spin order inherent in parahydrogen is quantitatively transferred to the precursor, with subsequent generation of the hyperpolarized $^{13}C$ imaging reagent for injection into an animal or biological test system held within a conventional NMR spectrometer.

With the present apparatus, high levels of hyperpolarization permitted early in vivo studies, which proved the potential of hyperpolarized $^{13}C$ MRI in biology [Golman K. et al., *Parahydrogen-induced polarization in imaging: subsecond*

C-13 *angiography*. Magn Reson Med 46: (2001) 1-5]. Ideally, and within a few minutes, the process is repeated, with the same or very comparable volume and hyperpolarization of the product. The PASADENA polarizer described herein advances upon the prototype described briefly by Axelsson et al. [Golman K. et al., *Parahydrogen-induced polarization in imaging: subsecond C-13 angiography*. Magn Reson Med 46: (2001) 1-5] (GE/Amersham, Malmö, Sweden). It is designed to be reliable, low cost and to produce hyperpolarized biomolecules in solution quickly and efficiently in amounts applicable for biological use. Additionally, unlike previous polarizers, which required the constant attention of 4-5 dedicated and highly trained individuals and was variable in its performance, a single person can operate the subject matter apparatus after a single demonstration. Combined with Quality Assurance ("QA") methods, described herein, the subject matter PASADENA polarizer and methods for using such are shown to provide reproducible hyperpolarization of biomolecules at $P=[15.3\pm1.9]\%$, where P stands for a polarization rate.

SUMMARY OF THE SUBJECT MATTER

The subject matter disclosed herein teaches systems and apparatus for improving imaging quality via hyperpolarization (e.g., a PASADENA polarizer) intended to perform the steps of generation, chemistry and hardware of the hydrogenation reaction, and the MRI electronics associated with the spin order transfer. The subject matter further discloses methods for performing such hyperpolarization including quality assurance procedures necessary for the setup and optimization of polarization yield, and operational protocols developed for efficient day-to-day operation of the subject matter apparatus (e.g., a PASADENA polarizer).

In one aspect, the subject matter provides a system and/or an apparatus for hyperpolarization. In some embodiments, the system/apparatus comprises a reaction chamber for hyperpolarization; a transmitter device for transmission of radio frequency (R.F.) pulses into the reaction chamber; a static magnetic field generator for generating a static magnetic field surrounding the reaction chamber; and a plurality of valves employed for fluid and/or gas flow and delivery to and from the reaction chamber; where an image reagent solution is introduced, via one of the valves in the plurality, into and hyperpolarized within the reaction chamber. In some and rare embodiments, only one value is employed for fluid and/or gas flow and delivery to and from the reaction chamber.

In some embodiments, the system/apparatus further comprises a power source for supplying power to the transmitter device and the static magnetic field generator.

In some embodiments, the system/apparatus further comprises a central processor, where the central processor controls the plurality of valves employed for fluid flow and delivery of an image reagent solution to and from the reaction chamber for hyperpolarization.

In some embodiments, the system/apparatus further comprises an image reagent solution source in communication with the reaction chamber for supplying the image reagent solution.

In some embodiments, the system/apparatus further comprises a parahydrogen generator in communication with the reaction chamber for generating and delivering parahydrogen.

In some embodiments, the system/apparatus further comprises a nitrogen source in communication with the reaction chamber for supplying nitrogen.

In some embodiments, the system/apparatus further comprises a Hall sensor for monitoring the strength and stability of the power source. In some embodiments, the Hall sensor is located between the transmitter device and the reaction chamber.

In some embodiments, at least one valve in the plurality is composed of a material independently selected from, for example, polytetrafluoroethylene, perfluoroalkoxy polymer resin, fluorinated ethylene-propylene, fluoropolymer, fluorocarbon, polysulfone, or a combination thereof. In some embodiments, more than one valves in the plurality are composed of a material independently selected from, for example, polytetrafluoroethylene, perfluoroalkoxy polymer resin, fluorinated ethylene-propylene, fluoropolymer, fluorocarbon, polysulfone, or a combination thereof. In some embodiments, each valve in the plurality is composed of a material independently selected from, for example, polytetrafluoroethylene, perfluoroalkoxy polymer resin, fluorinated ethylene-propylene, fluoropolymer, fluorocarbon, polysulfone, or a combination thereof.

In some embodiments, at least one valve in the plurality is an electromagnetic solenoid valve. In some embodiments, more than one valves in the plurality are electromagnetic solenoid valves. In some embodiments, all valves in the plurality are electromagnetic solenoid valves.

In some embodiments, at least one valve in the plurality is a pinch valve. In some embodiments, more than one valves in the plurality are pinch valves. In some embodiments, all valves in the plurality are pinch valves.

In some embodiments, combinations of valves (e.g., solenoid and pinch valves) are used.

In some embodiments, application of the transmitter device and static magnetic field generator in conjunction with the handling of the image reagent solution is controlled by a central processor.

In some embodiments, the system/apparatus further comprises a synthesizer in communication with the transmitter device for facilitating radio frequency pulse transmission.

In another aspect, the subject matter also provides a method for performing a hyperpolarization process to improve imaging quality, in particular, the quality of magnetic resonance imaging. In some embodiments, the method comprises reacting an image reagent solution with parahydrogen in a reaction chamber to form a hyperpolarized product, wherein the image reagent solution comprises a precursor molecule and a catalyst: transmitting radio frequency (R.F.) pulses, via a transmitter device, into the reaction chamber to enact a spin-order transfer sequence in the hyperpolarized product; and generating, via a static magnetic field generator, a static magnetic field surrounding the reaction chamber.

In some embodiments, the method further comprises providing parahydrogen to the reaction chamber.

In some embodiments, the method further comprises producing the image reagent solution.

In some embodiments, the method further comprises introducing the image reagent solution into the reaction chamber.

In some embodiments, the method further comprises supplying power, via a power source, to the transmitter device and static magnetic field generator.

In some embodiments, the method further comprises ejecting the hyperpolarized product from the reaction chamber.

In some embodiments, the method further comprises filtering the hyperpolarized product to remove the catalyst.

In some embodiments, the method further comprises introducing the filtered hyperpolarized product into a biological subject.

In some embodiments, the method further comprises exposing the biological subject to a high-field nuclear magnetic resonance spectrometer.

In some embodiments, the precursor molecule of the image reagent solution comprises carbon-13, nitrogen-15, oxygen-18, or a combination thereof.

In some embodiments, a central processor is used to control the handling of the imaging reagent solution and parahydrogen.

In some embodiments, the method further comprises flushing the reaction chamber prior to and/or after a reaction between the imaging reagent solution and parahydrogen.

In some embodiments, the method further comprises calibrating of the nuclear magnetic resonance spectrometer.

In some embodiments, the method further comprises determining a center frequency of the nuclear magnetic resonance spectrometer.

In some embodiments, the method further comprises calibrating the radio frequency pulses of the transmitter device.

In some embodiments, the method further comprises determining J-couplings for the imaging reagent solution.

In some embodiments, the method further comprises calibrating spin order transfer for the static magnetic field generator by hyperpolarization.

In some embodiments, the method further comprises calibrating spin order transfer for the transmitter device by hyperpolarization.

In some embodiments, the method further comprises utilizing Insensitive Nuclei Enhanced by Polarization Transfer (INEPT) sequence to transfer the hyperpolarized product to proton ($^1H$).

In some embodiments, the method further comprises monitoring, via a Hall sensor, the strength and stability of the power source. In some embodiments, the Hall sensor is located between the transmitter device and the reaction chamber.

In some embodiments, the method further comprises facilitating radio frequency pulse transmission, via a synthesizer, into the reaction chamber, wherein the synthesizer is in communication with the transmitter device.

In some embodiments, the method further comprises generating and delivering parahydrogen, via a parahydrogen generator, into the reaction chamber, wherein the reaction chamber is in communication with the reaction chamber.

One of skill in the art will understand that not all steps mentioned above need to be included in a process of hyperpolarization. In some embodiments, multiple steps in the process can occur at the same time. For example, the ejection of hyperpolarized product from the reaction chamber and filtration of the same product can take place as the same time when, for example, the outlet of the reaction chamber contains a built-in filter.

It will also be understood by one of skill in the art, that the same method step can take place multiple times to further improve efficiency. For example, r.f. can be introduced at multiple time intervals into the reaction mix. Similarly, filtration can also take place multiple times to ensure purity.

In some embodiments, at least one valve in the plurality is composed of a material independently selected from, for example, polytetrafluoroethylene, perfluoroalkoxy polymer resin, fluorinated ethylene-propylene, fluoropolymer, fluorocarbon, polysulfone, or a combination thereof. In some embodiments, more than one valves in the plurality are composed of a material independently selected from, for example, polytetrafluoroethylene, perfluoroalkoxy polymer resin, fluorinated ethylene-propylene, fluoropolymer, fluorocarbon, polysulfone, or a combination thereof. In some embodiments, each valve in the plurality is composed of a material independently selected from, for example, polytetrafluoroethylene, perfluoroalkoxy polymer resin, fluorinated ethylene-propylene, fluoropolymer, fluorocarbon, polysulfone, or a combination thereof.

In some embodiments, at least one valve in the plurality is an electromagnetic solenoid valve. In some embodiments, more than one valves in the plurality are electromagnetic solenoid valves. In some embodiments, all valves in the plurality are electromagnetic solenoid valves.

In some embodiments, at least one valve in the plurality is a pinch valve. In some embodiments, more than one valves in the plurality are pinch valves. In some embodiments, all valves in the plurality are pinch valves.

In some embodiments, combinations of valves (e.g., solenoid and pinch valves) are used.

In some embodiments, a central processor controls the handling of the image reagent solution and application of the transmitter device and the static magnetic generator.

The present subject matter also provides a computer system that comprises a processor, and a memory coupled to the processor. The computer encodes one or more programs which cause the processor to carry out the method of any one of the methods described herein.

The present subject matter further provides a computer program product for use in conjunction with a computer having a processor and a memory connected to the processor. The computer program product comprises a computer readable storage medium on which a computer program mechanism is encoded. The computer program mechanism may be loaded into the memory of the computer and cause the computer to carry out the method of any one of the methods described herein.

The system of the subject matter is broadly defined. For example, a system can include multiple apparatuses, in addition to any conventionally available equipments, apparatuses and/or material to perform the functions described herein. It will also be understood by one of skill in the art that, in some embodiments, one apparatus is provided that performs the functions described herein. In some embodiments, more than one apparatuses are used to perform the functions described herein.

BRIEF DESCRIPTION OF THE FIGURES

Exemplary embodiments are illustrated in referenced figures and tables. It is intended that the embodiments, figures and tables disclosed herein are to be considered illustrative rather than restrictive. The dimensions shown in various figures are in millimeters.

FIG. 3a. A schematic view of the PASADENA $B_1$ R.F. transmission coil.

FIG. 3b. A picture of the PASADENA $B_1$ R.F. transmission coil.

Table 1. Shows the components of the fluid control unit.
Table 2. Shows the components of the low field NMR unit.
Table 3. Shows the components of the process control unit.
Table 4. Shows the components of the parahydrogen generator.
Table 5. Shows the corresponding chemicals and axillaries.
Table 6. Shows the workflow of the PASADENA polarizer.
Table 7. Shows the protocol for PASADENA hyperpolarization.
Table 8. Shows the reproducibility and performance of the PASADENA polarizer.
Table 9. Shows the source of materials used in experimental design.

DETAILED DESCRIPTION OF THE SUBJECT MATTER

All references cited herein are incorporated by reference in their entirety as though fully set forth.

Unless defined otherwise, technical and scientific terms used herein have the same meaning as commonly understood by one of ordinary skill in the art to which the subject matter belongs. Singleton et al., Dictionary of Microbiology and Molecular Biology 3rd ed., J. Wiley & Sons (New York, N.Y. 2002); March, Advanced Organic Chemistry Reactions, Mechanisms and Structure 4th ed., J. Wiley & Sons (New York, N.Y. 1992); and Culbreth L. J., Watson C., Magnetic Resonance Imaging Technology, W.B. Saunders Company (2009), provide one skilled in the art with a general guide to many of the terms used in the present application.

While the description below refers to particular embodiments of the present subject matter, it should be readily apparent to people of ordinary skill in the art that a number of modifications may be made without departing from the spirit thereof, including the use of alternate materials, components, mechanisms, compositions. The accompanying claims are intended to cover such modifications as would fall within the true spirit and scope of the subject matter. All changes that come within the meaning of and range of equivalency of the claims are intended to be embraced therein The subject matter disclosed herein teaches the subject matter apparatus for improving imaging quality via hyperpolarization (e.g., a PASADENA polarizer) intended to perform the steps of generation, chemistry and hardware of the hydrogenation reaction, and the MRI electronics associated with the spin order transfer. The subject matter further discloses methods for performing such hyperpolarization including quality assurance procedures necessary for the setup and optimization of polarization yield, and operational protocols developed for efficient day-to-day operation of the subject matter apparatus (e.g., a PASADENA polarizer).

PASADENA Polarizer

Figure 1A:
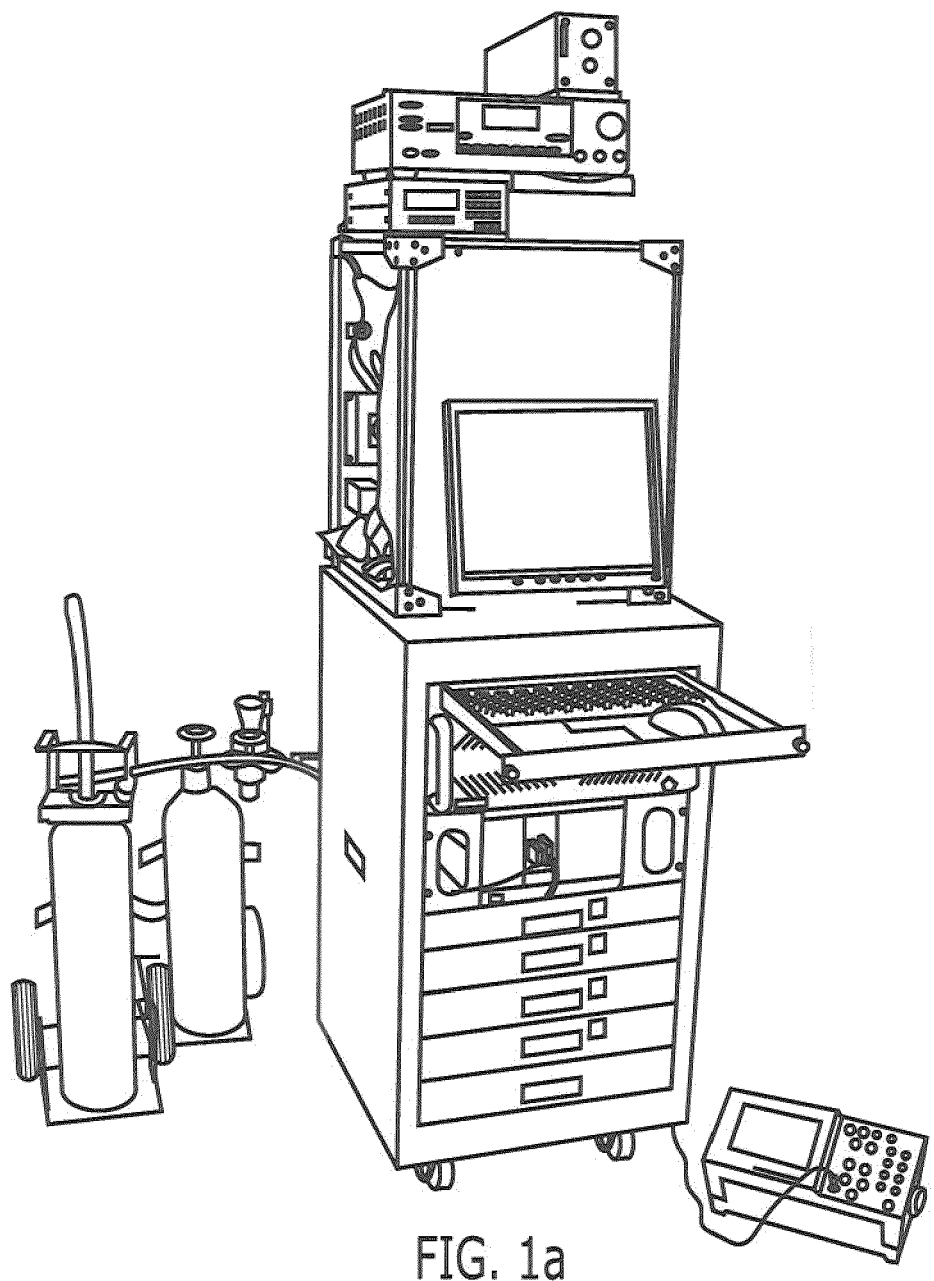
FIG. 1a. A picture of the PASADENA polarizer.
Figure 1B:
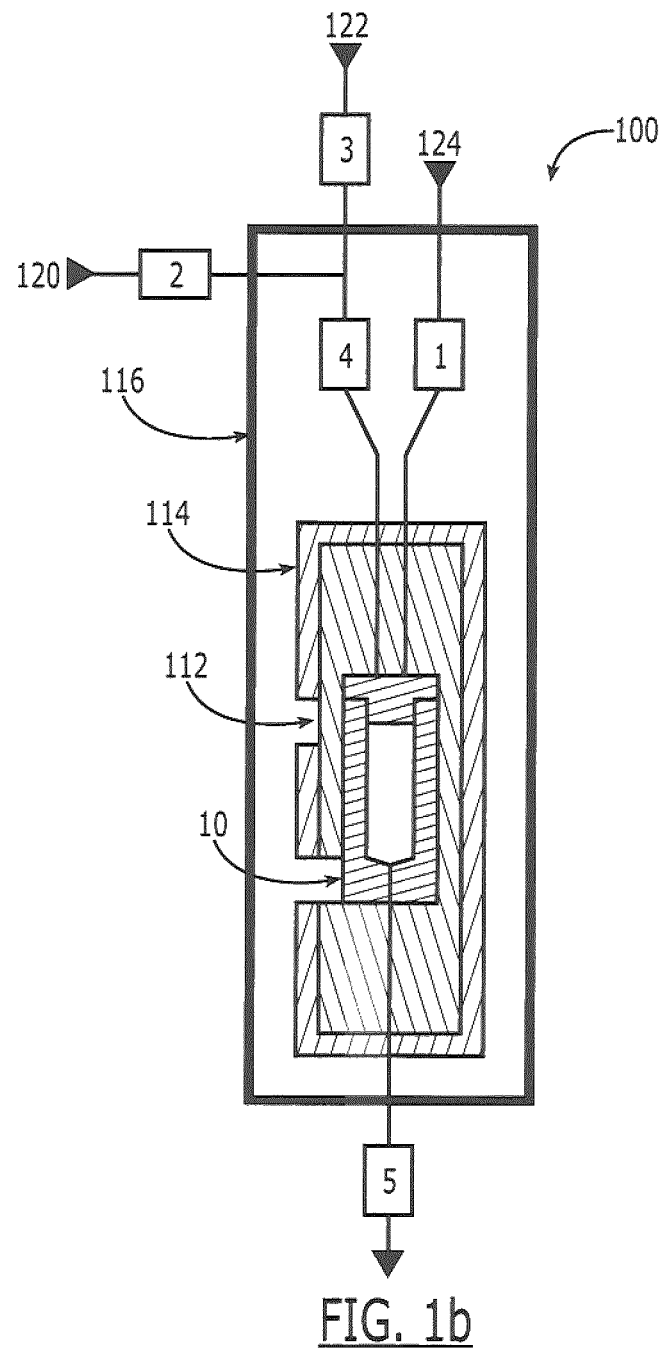
FIG. 1b. A schematic view of the PASADENA polarizer.

Systems and methods for providing reproducible and efficient hyperpolarization of biomolecules are provided. Exemplary embodiments are depicted in FIGS. 1a and 1b. It will be understood by one of skill in the art that the exemplary embodiments discussed herein are provided by way of illustration and should not be used to limit the scope of the subject matter.

In one aspect, functional components of an exemplary embodiment of the subject matter (e.g., polarizer 100) includes a hydrogenation compartment (e.g., reaction chamber or reactor 110), a transmitter device for transmitting r.f. pulses ($B_1$) (e.g., coil 112), and a static magnetic field generator ($B_0$) (e.g., an electromagnet 114). As used herein, the transmitter device is broadly defined as any device that is capable of transmitting r.f. Similarly, the static magnetic field generator is broadly defined as any device that is capable of generating a static magnetic field, including for example, an electromagnet.

In some embodiments, one or more of the functional components are included within a temperature control unit (e.g., a heating unit or chamber 116 in FIGS. 1a and 1b). In some embodiments, all the functional components disclosed herein are included within a temperature control unit.

In some embodiments, systems of the subject matter further include a computer interface. For example, computer interface 130 controls the experimental sequence of fluids and NMR. In some embodiments, the entire apparatus of a system of the subject matter is contained in a mobile housing located a distance (e.g., 7.6±0.1 m) from an unshielded 4.7 T magnet (stray field 0.1 mT). In some embodiments, appropriate r.f. and magnetic field shielding is provided. The distance could be further reduced, with the aim of minimizing the delivery time from the polarizer outlet to the imaging target within the MRI system.

In another aspect, the present subject matter can be implemented as a computer system and/or a computer program product that comprises a computer program mechanism embedded in a computer readable storage medium. Any known computer systems can be used to implement the subject matter. Further, any of the methods of the present subject matter can be implemented in one or more computers or computer systems. Further still, any of the methods of the present subject matter can be implemented in one or more computer program products. Some embodiments of the present subject matter provide a computer system or a computer program product that encodes or has instructions for performing any or all of the methods disclosed herein. Such methods/instructions can be stored on a CD-ROM, DVD, magnetic disk storage product, or any other computer readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. Such methods encoded in the computer program product can also be distributed electronically, via the Internet or otherwise, by transmission of a computer data signal (in which the software modules are embedded) either digitally or on a carrier wave.

Some embodiments of the present subject matter provide a computer system or a computer program product that contains any or all of the program modules as disclosed herein. These program modules can be stored on a CD-ROM, DVD, magnetic disk storage product, or any other computer readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal (in which the software modules are embedded) either digitally or on a carrier wave.

In some embodiments, systems of the subject matter further include a parahydrogen generator unit, which is necessary for the discontinuous production of parahydrogen of high purity (97-100%). In some embodiments, the parahydrogen generator unit can be located off-site, with only sufficient gas held in a transport cylinder on site, for a full day of operation of the polarizer.

An exemplary process (e.g., by operating a PASADENA polarizer) entails rapid mixing and chemical interaction between parahydrogen, a $^{13}C$ (or $^{15}N$) enriched precursor, and a catalyst in the correct proportions in a heated chamber located within a low field NMR spectrometer. The high spin order inherent in parahydrogen is quantitatively transferred to a precursor, with subsequent recovery of the hyperpolarized $^{13}C$ MR imaging reagent for injection into a biological subject held within a conventional high-field NMR spectrometer [M. Goldman et al., *Design and implementation of C-13 hyperpolarization from para-hydrogen, for new MRI contrast agents*. Comptes Rendus Chimie 9 (2006) 357-363]. Such hyperpolarization permitted early in vivo studies which proved the potential of hyperpolarized $^{13}C$ MRI in biology [K. Golman et al., *Parahydrogen-induced polarization in imaging: Subsecond C-13 angiography*. Magnetic Resonance in Medicine 46 (2001) 1-5; M. Goldman et al., *Hyperpolarization of C-13 through order transfer from parahydrogen: A new contrast agent for MRI*. Magnetic Resonance Imaging 23 (2005) 153-157].

In some embodiments, toxicity testing is conducted to ensure the safety of the reactants prior to and after the reaction. In some embodiments, a dosage analysis is used for toxicity testing.

In preferred embodiments, the reaction process is repeated within a few minutes rendering identical or very comparable results for volume and hyperpolarization of the product. Advantageously, the functional components of the subject matter comprise a laminar flow reaction chamber, a $B_1$ coil to transmit radio frequency (R.F.) pulses, and a $B_0$ electromagnet coil for generating a homogeneous static magnetic field. The $B_0$ and $B_1$ coils provide a low-field NMR unit. Tubes and valves are employed for diffusion of the imaging reagents which may be controlled by a computer.

In some embodiments, an apparatus of the subject matter (e.g., the PASADENA polarizer) is contained in a mobile housing cabinet (e.g., a Polarizer Cabinet as depicted in FIG. 1a) located 1 to 10 meters from an unshielded 4.7 T magnet (stray field 0.5 mT) of an MR spectrometer. With appropriate electromagnetic shielding, the distance can be reduced to 5 meters or less, 3 meters or less, 2 meters or less, 1 meter or less, 0.5 meter or less, or 0.2 meter or less. Additional details on methods and systems of magnetic shielding are also provided later herein.

With appropriate R.F. and magnetic field shielding, this distance may be altered, with the aim of minimizing the delivery time from the polarizer outlet to the imaging target within the MR spectrometer. A parahydrogen generator, used for intermittent production of parahydrogen of high (97-100%) purity, may be located within close proximity of the mobile housing or can be located off-site with only sufficient gas held in a transport cylinder on site, for operation of the polarizer.

A more complete exemplary process can be described in connection with the exemplary apparatus depicted in FIG. 1b. In FIG. 1b, exemplary ports for fluid control are marked by numbers (1)-(5). For example, a precursor sample 120, e.g., a $^{13}C$-enriched precursor-molecule (2) together with the catalyst in aqueous or deuterium solution (3), is added to the system by injection with a compressed non-reactive gas 122 (e.g., Nitrogen, Helium, Neon, Argon, Krypton, Xenon, Radon) through a port (4), then transported through clean, sterile plastic tubing by a system of pumps and valves. Precursor sample 120 then resides briefly in a heating unit 116 wound in an ante-chamber and is delivered to reaction chamber 110 (e.g., a laminar-flow reaction chamber). Reaction chamber 110, which has two entry ports (1 and 4) and an outflow port (5), is centered within the $B_0$ coil 114 and $B_1$ coil 112 of the low-field NMR. The second reactant, parahydrogen 124, is delivered to reaction chamber 110 under pressure via port (1). While precursor 120, parahydrogen 124 and catalyst are held in reaction chamber 110, a series of pulses played out in the $B_1$ coil 112 enacts a spin-order transfer sequence specific to the product of the hydrogenation reaction. The hyperpolarized product is ejected from reaction chamber 110 under the pressure of nitrogen gas 122, filtered to remove the catalyst and injected into an animal, organ or cell preparation previously mounted in the bore of a recording high-field NMR spectrometer (not shown in FIG. 1b).

A trigger encoded by the polarizer initiates in vitro or in vivo acquisitions which are completed within 5×T1 of injection of the hyperpolarized contrast reagent. Each cycle of hyperpolarization can complete in less than 1 minute (e.g., 52 seconds, as shown in Table 6). In preferred embodiments, the entire procedure including hyperpolarization, imaging, rinsing and reloading the polarizer with precursor, occupies a few minutes (e.g., 182 seconds as shown in Table 6).

1. Fluid Control Unit

Reaction Chamber

In some embodiments, reaction chamber 110 is made of glass, ceramic, plastics, metal, metal alloy, or a combination thereof. One of skill in the art would understand that the characteristics of reaction chamber 110 will be determined by the properties of the reactants and the reactions (e.g., pressure, temperature, pH level, etc.). For example, plastics used to made reaction chamber 110 can include a urethane polymer, an acrylic polymer, a fluoropolymer, polybenzamidazole, polymide, polytetrafluoroethylene, polyetheretherketone, polyamide-imide, glass-based phenolic, polystyrene, cross-linked polystyrene, polyester, polycarbonate, polyethylene, polyethylene, acrylonitrile-butadiene-styrene, polytetrafluoro-ethylene, polymethacrylate, nylon 6.6, cellulose acetate butyrate, cellulose acetate, rigid vinyl, plasticized vinyl, or polypropylene or a combination thereof. Also, for example, glass material used to made reaction chamber 110 can include alumino-silicate glass, borosilicate glass, dichroic glass, germanium/semiconductor glass, glass ceramic, silicate/fused silica glass, soda lime glass, quartz glass, chalcogenide/sulphide glass, fluoride glass, flint glass, cereated glass or a combination thereof.

Figure 2A:
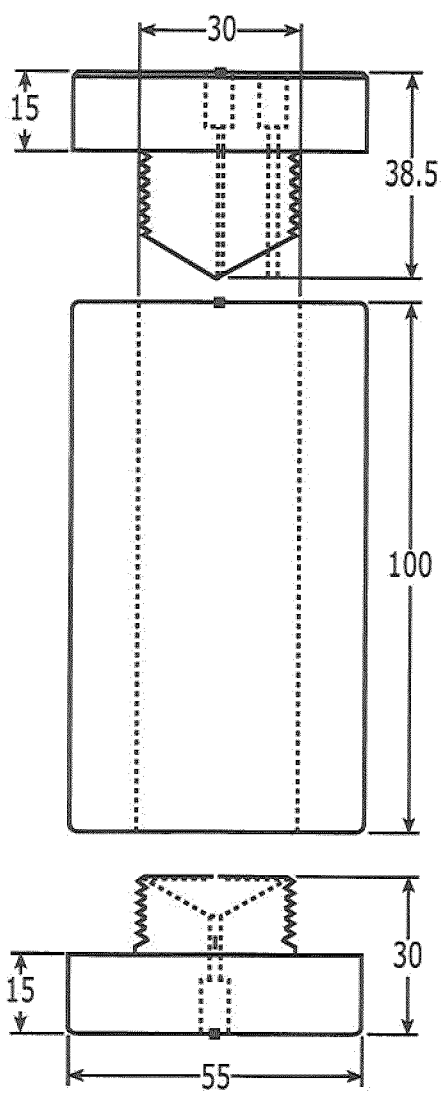
FIG. 2a. A schematic view of the PASADENA laminar-flow reaction chamber.
Figure 2B:
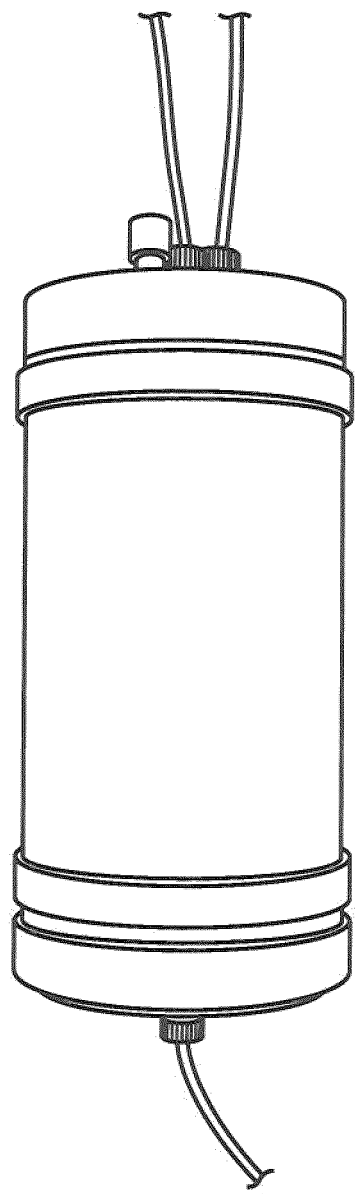
FIG. 2b. A picture of the PASADENA laminar-flow reactor.
Figure 4A:
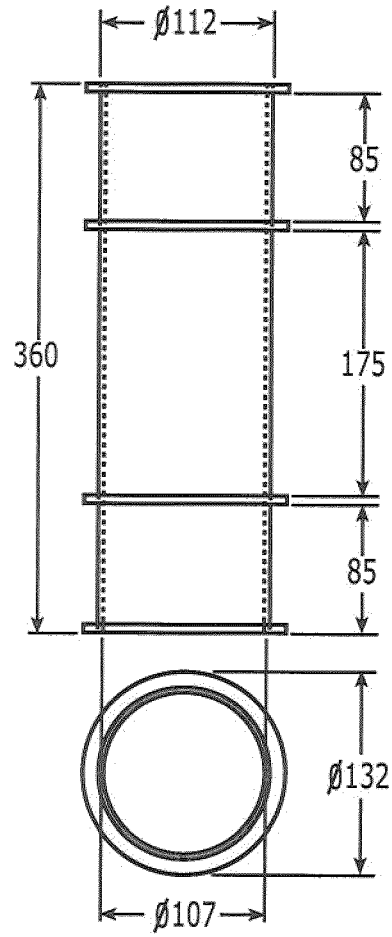
FIG. 4a. A schematic view of the PASADENA solenoid coil.
Figure 4B:
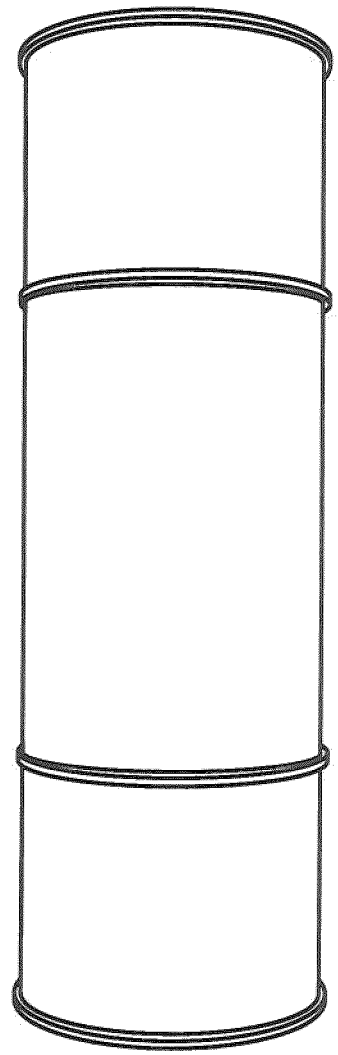
FIG. 4b. A picture of the PASADENA solenoid coil.
Figure 4C:
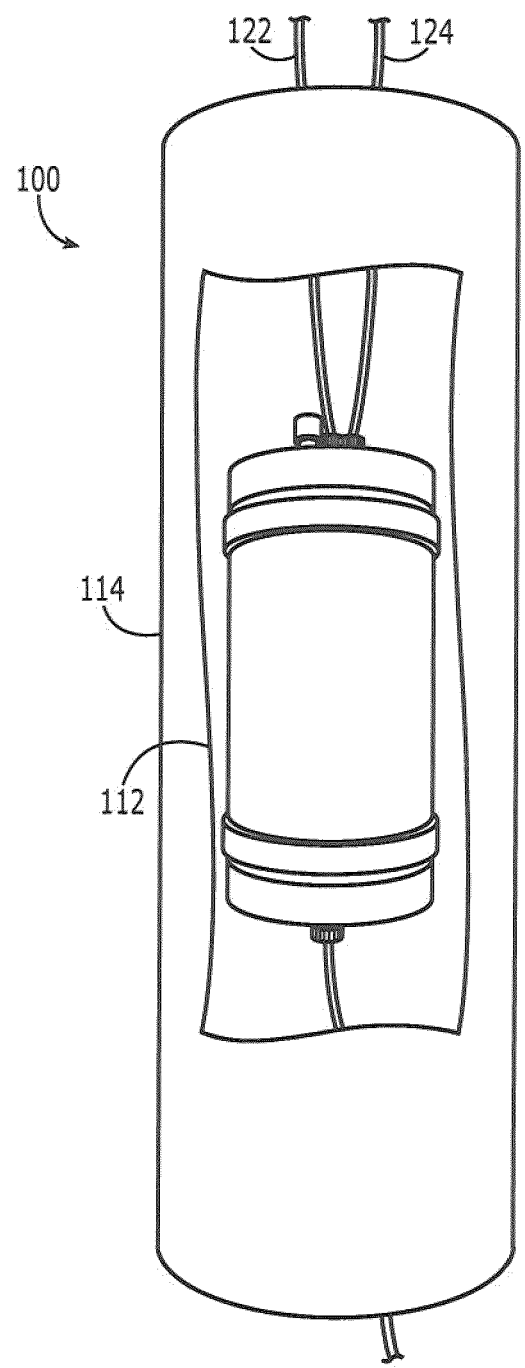
FIG. 4c. A picture of the complete assembly of the parts described in FIGS. 2, 3 and 4.

In an exemplary embodiment as depicted in FIG. 2, reaction chamber 110 (in the shape of a right cylinder) is machined from polysulfone plastic to withstand pressure in excess of 15 bar and temperature exceeding 70° C. Exemplary dimensions of reaction chamber 110 are also provided.

One of skill in the art would understand that the reaction chamber can be of any shape. Advantageously, reaction chamber 110 is near cylindrical in shape.

In some embodiments, the internal surface of reaction chamber 110 is coated with a protective layer to prolong its life span and/or facilitate quantitative handling of the reactions within reaction chamber 110.

In some embodiments, reactants (e.g., solvent, precursor molecule) are mixed to cause the desired reaction in liquid form with the parahydrogen. In a preferred embodiment, reaction chamber 110 is a laminar-flow chamber. In alternative embodiments, reactants are mixed to cause the desired reaction in vapor or mist form.

In some embodiments, reaction chamber 110 includes a mechanism for complete mixing of the reactants to ensure complete reaction. Exemplary mixing mechanisms include but are not limited to mixing by vortexing, blending, and shaking. In some embodiments, beads are added to the reactants for mixing purposes.

In some embodiments, the reactants are repeatedly delivered into the reaction chamber at a reasonable time interval to facilitate the reaction. For example, the reactants can be delivered twice or more, three times or more, four times or more, five times or more, six times or more, seven times or more, eight times or more, nine times or more, or ten times or more. In some embodiments, reactants are added sequentially while in other embodiments, reactants are added simultaneous.

In some embodiments, reaction chamber 110 consists of three sections, the injection cap, reactor body, and extraction cap. In some embodiments, these three sections are made from any of the material listed herein or deemed reasonable by one of skill in the art based on the desired reaction. In some embodiments, all three sections are machined from polysulfone plastic. In some embodiments, both caps are disc-shaped, and include an externally threaded section which mates with a respective internally threaded section in the reactor body. In some embodiments, the caps are snapped onto the reactor body. Each cap is seal to a respective end of the reactor body, for example, via one or more O-rings. In some embodiments, a sealant and/or an adhesive is applied to facilitate the connection between the caps and the reactor body, including but not limited to silicone, ethylene vinyl acetate.

In some embodiments, the injection cap includes a central bore for the injection of a stream of liquid precursor solution. The injection cap also includes a laterally offset bore for the injection of nitrogen or parahydrogen. The central bore has a diameter of approximately 0.5 mm, with the diameter of the offset bore being substantially larger. The surface of the inner end of the threaded section of the injection cap is conically shaped to slope down and inward. The surface of the inner end of the threaded section of the extraction cap slopes down and inward to form a funnel-shaped floor, which allows for ejection of the hyperpolarized product through a vertical stepped central bore extending through the extraction cap. In some embodiments, the injection cap includes a device that pressurizes and/or vaporizes liquid precursor solution as it enters the reaction chamber. In preferred embodiments, the reaction chamber is constructed of plastic to optimize flow and mixing of reagents and gases, as well as to allow rapid evacuation and complete rinsing between each use of the polarizer. Plastic construction also permits repeated use of the polarizer through cycles of extreme pressure and temperature changes without loss of structural integrity.

In an alternative embodiment, the injection cap or the extraction cap can be formed integrally with the reactor body. Exemplary details of the auxiliary equipment, heater, fan, injection port and delivery system are given in Table 1.

Valves and Tubing for Fluids

In some embodiments, fluid flow is controlled by electromagnetic solenoid valves connected by polytetrafluoroethylene ("PTFE") tubing and matching nuts with ferrules. In some embodiments, a PTFE sleeve in the valves prevents liquids from coming into contact with metal (Table 1), thereby permitting use of acidic reagents.

In some embodiments, advantageously, one or more pinch valves are used. A pinch valve is a full bore or fully ported type of control valve which uses a pinching effect to obstruct fluid flow. Exemplary types of pinch valves include but are not limited to fluid pinch valves; air operated pinch valves. Exemplary material for constructing valves of the subject matter include synthetic or natural rubber, metal, plastics, EPDM, nitrile, viton, neoprene and butyl or a combination thereof.

Additional types of valves include but are not limited to hydraulic, pneumatic, and manual valves. Exemplary valves further include but are not limited to a ball valve, for on/off control without pressure drop, and ideal for quick shut-off since a 90° turn offers complete shut-off angle, compared to multiple turns required on most manual valves; a butterfly valve, for flow regulation in large pipe diameters; a ceramic Disc valve, used mainly in high duty cycle applications or on abrasive fluids; a check valve or non-return valve, allows the fluid to pass in one direction only; a hastelloy check valve; a choke valve, a valve that raises or lowers a solid cylinder which is placed around or inside another cylinder which has holes or slots. Used for high pressure drops found in oil and gas wellheads; a diaphragm valve, some are sanitary predominantly used in the pharmaceutical and foodstuff industry; a gate valve, mainly for on/off control, with low pressure drop; a stainless steel gate valve; a globe valve, for regulating flow; a knife valve, for slurries or powders on/off control; a needle valve for accurate flow control; a piston valve, for regulating fluids that carry solids in suspension; a plug valve, slim valve for on/off control but with some pressure drop; a poppet valve; spool valve, for hydraulic control; a thermal expansion valve, used in refrigeration and air conditioning systems; or any suitable valve known to one of skill in the art.

In some embodiments, a combination of valves can be used. For example, a liquid valve can be used to deliver imaging solution while a valve for suitable for air can be used to deliver parahydrogen.

Ante Chamber

In some embodiments, the fluid control unit further includes PTFE tubing coiled within a variable heating element capable of reaching 80° C., leads from the injection port to the reaction chamber (e.g., a laminar-flow reaction chamber).

Heating Unit

In some embodiments, systems of the subject matter include a heating unit or chamber 116 for reaction chamber 110. Referring to FIG. 1b, the dotted rectangle (116) can be an enclosure of any suitable non-magnetic material (e.g., aluminum, or plastic which will handle the temperature required for the reaction chamber), and the hot air source shown as connected to it by non-magnetic ducts long enough to avoid interference from any stray magnetic fields which may come from the heater and blower.

In some embodiments, the antechamber of the subject matter is heated by hot air that is generated by a heating element outside of the ante chamber. The heating element is composed of two heated coils and, an internal fan continuously blows the heated air into the antechamber. The heating element is commercially available and can be bought from any electrical clothes dryer parts distributor.

In some embodiments, the temperature of the ante chamber is monitored by a thermostat positioned next to the reactor. In some embodiments, the temperature is controlled by a digital micro-temperature controller (Omega Engineering CN132). In some embodiments, the temperature within the ante chamber can be changed manually to any temperature between 30° C. to 80° C. This setup has been shown to produce uniform heat within the ante chamber and to be stable during the use of the apparatus (e.g., a PASADENA polarizer). Whether monitored by electronically and automatically or manually, the temperature of the ante chamber is maintained 0° C. to 100° C.; 10° C. to 90° C.; 10° C. to 80° C.; 20° C. to 80° C.; 30° C. to 80° C.; 40° C. to 80° C.; 50° C. to 80° C.; 60° C. to 80° C.; 60° C. to 80° C.; 10° C. to 20° C.; 20° C. to 30° C.; 20° C. to 40° C.; 20° C. to 50° C.; 20° C. to 60° C.; 20° C. to 70° C.; 20° C. to 80° C.; 20° C. to 90° C.; 30° C. to 40° C.; 30° C. to 50° C.; 30° C. to 60° C.; 30° C. to 60° C.; 30° C. to 80° C.; 30° C. to 90° C. In some embodiments, reaction temperature is higher than 90° C.; 100° C. or higher; 150° C. or higher; or 200° C. or higher. In some embodiments, a temperature profile is used to control and change temperature through a process of the subject matter.

In some embodiments, the catalyst solution containing the compound to be polarized is initially heated in PTFE tubing with an inner volume (e.g., 5 ml) that is coiled within the heated ante chamber between the injection port (2) and the intake valve (4) of the laminar flow reaction chamber.

In some embodiments, the precursor solution is sterilized. In some embodiments, sterilization of the precursor solution is achieved by using high percentage and safe sterilizing reagents such as ethanol and/or iso-propanol. In some embodiments, sterilization is achieved by using disposable reactor chambers; tubings, and/or valves.

In some embodiments, automated production of sterilized precursor solution is provided. In some embodiments, a separate apparatus is used to automatically produce sterilized precursor solution. In some embodiments, the production of precursor solution is continuous or at regular time intervals.

It will be understand by one of skill in the art that any material described herein or known in the art can be used to construct the reaction chamber, ante chamber, valves and tubing, caps, heating unit, and/or any auxiliary equipment.

2. NMR Unit of the Polarizer

In some embodiments, systems and apparatus of the subject matter include a low-field NMR unit of the polarizer (FIG. 3) for performing the spin order transfer sequence, concurrently with hydrogenation of the precursor molecule with parahydrogen [M. Goldman et al., *Hyperpolarization of C-13 through order transfer from parahydrogen: A new contrast agent for MRI*. Magnetic Resonance Imaging 23 (2005) 153-157; M. Goldman, and H. Johannesson, *Conversion of a proton pair para order into C-13 polarization by r.f. irradiation, for use in MRI*. Comptes Rendus Physique 6 (2005) 575-581]. In some embodiments, the static magnet field generator ($B_0$) and transmitter device for transmitting r.f. pulses ($B_1$) fields are located around the reaction chamber (FIG. 2). In some embodiments, coils and/or solenoids are used as $B_0$ and $B_1$. Any suitable means for generating static magnetic field and/or transmitting r.f. can be used to create $B_0$ and $B_1$.

R.F. Transmission

Referring now to FIG. 3, in some embodiments, the transmitter device for transmitting r.f. pulses (e.g., $B_1$ coil) consists of two elements, e.g., as two saddle-shaped loops, each with six turns of appropriate gauge magnet wire mounted on opposite sides of a transparent acrylic plastic tube. Any plastic material described herein can be used to construct the tube upon which the magnet wire is mounted. In some embodiments, the two loops are connected in parallel to an r.f. source by flexible leads through a BNC connector in a removable cover on the upper end of the plastic tube. The reaction chamber rests on a movable horizontal annular acrylic disc at the iso-center of the saddle-shaped loops of the $B_1$ coil. The disc is held in place by screws threaded through the plastic tube and into the edge of the disc, which can be moved vertically to different locations in the tube to accommodate reactors of different sizes. The disc has four outward opening vertical slots to provide clearance for vertical portions of the saddle-shaped loops of the $B_1$ coil. The two saddle-shaped loops are symmetrically disposed about a common longitudinal access, which also includes the longitudinal axis of the reactor inlet and exit bores.

In alternative embodiments, the transmitter device for transmitting r.f. pulses includes 2 or more elements, 3 or more elements, 4 or more elements, 5 or more elements, 6 or more elements, 7 or more elements, 8 or more elements, each located adjacent to the reaction chamber to provide r.f. to the reactants. In some embodiments, these elements are identical or similar to each other. In some embodiments, these elements are not similar to each other. In some embodiments, these elements are positioned symmetrically or near symmetrically with respect to the reaction chamber. In some embodiments, these elements are not positioned symmetrically with respect to the reaction chamber. In some embodiments, the transmitter device for transmitting r.f. pulses consists only a single element and it is positioned, for example, surrounding the reaction chamber, in a ring-like structure. Alternatively, an opening is found in the ring-like structure.

Static Magnetic Field

Figure 5:
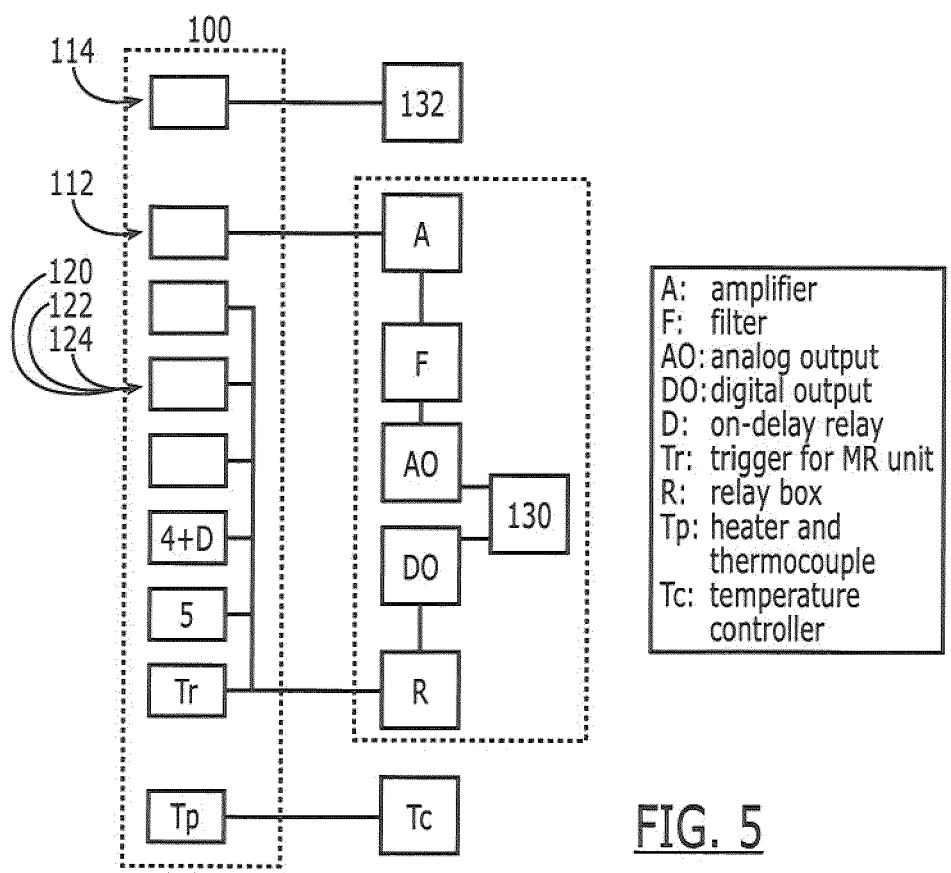
FIG. 5. A schematic view of the process control for the PASADENA polarizer.

In some embodiments, the static magnetic field generator 114 (e.g., $B_0$ coil) of the low field unit is generated by three separate, vertically stacked, collinear solenoid coils that surround the R.F. transmission ($B_1$) coil 112 and the reaction chamber 110 (FIG. 1 and FIG. 5). The ($B_1$) solenoid coils 112 are driven by a precision DC power supply 132. In some embodiments, the center solenoid coil is twice as long as each of the upper and lower coils. The strength and stability of the static magnetic field is monitored by a Hall sensor (Probe and Gaussmeter, Space 450, Lake Shore, USA), located between the $B_1$ coil and the reaction chamber. The sensor is located near the bottom of the reactor, which coincides with the iso-center of the assembly. To allow for independent and precise adjustment of the current flow through each solenoid coil, separate variable power resistors are connected in parallel with each solenoid. This improves low-field homogeneity and compensates for extraneous z gradients, originating from the proximity of the low field unit to the high-field NMR spectrometer, or from other sources in the laboratory.

In some embodiments, static magnetic field generator 114 comprises more than two solenoid coils; more than three solenoid coils; more than four solenoid coils; more than five solenoid coils; more than six solenoid coils; more than seven solenoid coils; more than eight solenoid coils; more than nine solenoid coils; more than ten solenoid coils. In some embodiments, these solenoid coils are stacked and/or collinear. In some embodiments, these solenoid coils are not stacked and/or collinear. In some embodiments, these coils are identical or similar to each other. In some embodiments, these coils are not similar to each other.

In some embodiments, static magnetic field generator 114 is positioned outside of the reaction chamber, and generates the static magnetic field. In some embodiments, these coils are positioned symmetrically or near symmetrically with respect to the reaction chamber. In some embodiments, these coils are not positioned symmetrically with respect to the reaction chamber. In some embodiments, the static magnetic field generator consists only a single coil and it is positioned, for example, surrounding the reaction chamber, in a ring-like structure. Alternatively, an opening is found in the ring-like structure. The exemplary arrangements of the static magnetic field generator and r.f. transmitter are provided herein by way of example. It will be understood by one of skill in the art that any number and/or arrangement may be used in the subject matter to facilitate the spin order transfer sequence, concurrently with hydrogenation of the precursor molecule with parahydrogen.

3. Process Control Unit:

R.F. Transmission (FIG. 5)

In some embodiments, the R.F. pulses necessary for the spin order transfer are delivered from a synthesizer mounted in the Polarizer Cabinet. Pulses were digitized at an update frequency of 300 kHz, with four sample points per period at the $^1H$ frequency, and >16 samples per period at the $^{13}C$ frequency. The signal then passed through a low-pass filter with a cut-off frequency of approximately 150 kHz, to an amplifier, and is applied to the un-tuned saddle-shaped loops of the $B_1$ coil. To facilitate R.F. calibrations, the amplitude of the R.F. output is variable (Table 3). The R.F. optimization is performed as described below. The amplitudes of the square pulses of 25V for carbon and 50V for hydrogen, resulted in pulse widths of 115 μs for an inversion pulse for 1H and 230 μs for an inversion pulse for 13C.

Hardware

The analog output of a DAC PXI card is used to generate waveforms of the R.F. sequence. The digital input/output channels of the DAC card are also connected to relays to control opening and closing of the electromagnetic solenoid valves of the fluid system (Table 3).

Software

In some embodiments, custom programs are developed to control the processes of the subject matter, for example, based on the LabView platform. In some embodiments, the main features include the control of the digital outputs for mechanized mixing, delivery and recovery of imaging products in the correct sequence and application of a R.F. sequence with precise timing. The R.F. sequence for each experiment is saved in a separate file and reloaded to the program in the form of an ASCII file as necessary.

4. Parahydrogen Generator

Figure 6:
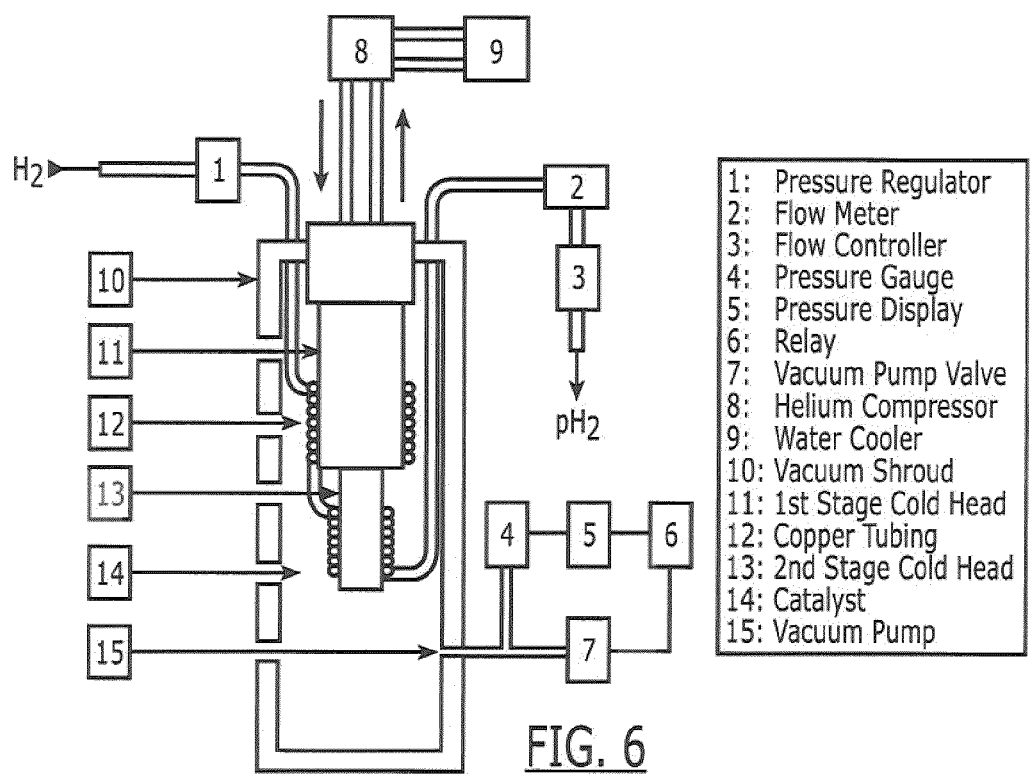
FIG. 6. A schematic view of a parahydrogen unit for the PASADENA polarizer
Figure 7:
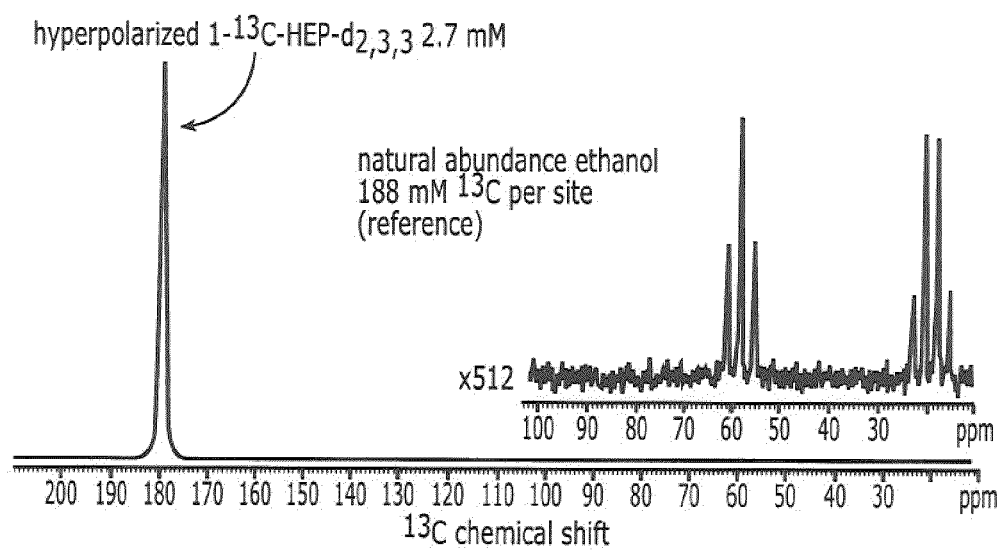
FIG. 7. A diagram representing the quantification of polarization achieved with the PASADENA polarizer.

The complete parahydrogen generator is represented diagrammatically in FIG. 6, with details of the components listed in Table 4. A similar setup was published by Tam et al. [S. Tam, and M. E. Fajardo, *Ortho/para hydrogen converter for rapid deposition matrix isolation spectroscopy*. Review of Scientific Instruments 70 (1999) 1926-1932]. Since the amount of hydrogen to be generated is relatively small, United States safety regulations, which apply to the production of four-hundred (400) or more liters hydrogen, is not applicable to a PASADENA polarizer.

5. Shielding Devices

In some embodiments, systems and/or apparatus of the subject matter are shielded from stray electro/electromagnetic/magnetic fields, such as those can be encountered in an MRI room when PASADENA is moved in there to be as close as possible to the patient when administering polarized compounds with a Short longitudinal relaxation T1.

Magnetic shielding is a process that limits the coupling of a magnetic field between two locations. Magnetic shielding is necessary because, unlike electricity, magnetic fields cannot be blocked or insulated. This is explained in one of Maxwell's Equations, del dot B=0, which means that there are no magnetic monopoles. Therefore, magnetic field lines must terminate on the opposite pole. There is no way to block these field lines; nature will find a path to return the magnetic field lines back to an opposite pole. This means that even if a nonmagnetic object—for example, glass—is placed between the poles of a horseshoe magnet, the magnetic field will not change. Instead of attempting to stop these magnetic field lines, magnetic shielding re-routes them around an object. This is done by surrounding the device to be shielded with a magnetic material. Magnetic permeability describes the ability of a material to be magnetized. If the material used has a greater permeability than the object inside, the magnetic field will tend to flow along this material, avoiding the objects inside. Thus, the magnetic field lines are allowed to terminate on opposite poles, but are merely redirected.

In some embodiments, magnetic shielding is achieved in conjunction with electro shielding. In some embodiments, magnetic shielding is achieved independently.

In some embodiments, magnetic shielding are achieved with a number of materials, including but not limited sheet metal, metal mesh, ionized gas, or plasma. The purpose of magnetic shielding is most often to prevent magnetic fields from interfering with electrical devices. For example, the most effective magnetic shielding material available is mumetal, an alloy of 77% nickel, 16% iron, 5% copper, and 2% chromium, which is then annealed in a hydrogen atmosphere to increase its permeability. In some embodiments, other alloys with similar compositions are sold for magnetic shielding, usually in rolls of foil, using, for example, a GIRON™ Magnetic Shielding Film; a magnetic shielding foil; a MagStop™ Plate; a Joint-Shield; a MetGlas™ Magnetic Shielding Film; a FINEMET® wide format film; a MagnetShield™ High Saturation Magnetic Alloy.

In some embodiments, only one level of shielding is used. In some embodiments, more than one levels of shielding are used. In some embodiments, shielding is used to isolate external magnetic fields. In some embodiments, shielding is used to isolate internal magnetic fields.

In some embodiments, for static or slowly varying magnetic fields (below about 100 kHz), shields made of high magnetic permeability metal alloys, such as large crystalline grain structure foils or sheet metals of Permalloy and Mumetal, are used to passively isolate a volume magnetically. Alternatively, nanocrystalline grain structure ferromagnetic metal coatings can be used. In some embodiments, the materials do not block the magnetic field, as with electric shielding, but rather draw the field into themselves, providing a path for the magnetic field lines around the shielded volume. Advantageously, a closed container is used as the best shape for magnetic shields.

In some embodiments, the effectiveness of this type of shielding decreases with the material's permeability, which generally drops off at both very low magnetic field strengths, and also at high field strengths where the material becomes saturated. In preferred embodiments, in order to achieve low residual fields, magnetic shields often consist of several enclosures one inside the other, each of which successively reduces the field inside it. In some embodiments, customdesigned shields are used for the subject matter (e.g., Amuneal Manufacturing Corp. Philadelphia, Pa.)

6. Chemicals and Ancillary Equipment

In preferred embodiments, a clean chemistry laboratory with a ventilation hood is desirable, as is an exhaust route for the gaseous products of the polarizer itself. While parahydrogen itself presents little hazard, reagents, solvents and catalysts employed in the systems and apparatus described herein (e.g., a PASADENA polarizer) are associated with a variety of volatile toxins. Table 5 lists the reagents, catalyst and solvents routinely employed. Suppliers are listed in Table 9. Additional examples are provided herein by way of illustration.

How to prepare chemistry and conduct a hyperpolarization experiment has been described herein under the heading "Quality Assurance."

The subject matter apparatus described herein has been in continuous use providing hundreds of effective hyperpolarizations with several different $^{13}C$ enriched reagents. Aside from the PASADENA polarizer's facility for use on biological subjects, favorable qualities and components of the subject matter are as follows:

1. The inventive apparatus does not use a metallic nozzle to spray reagent and parahydrogen into the reactor, because it is believed that simple mixing without contact with metals provides greater reproducibility in operation, and removes a cause of contamination and obstruction of flow. Moreover, the elimination of all metallic parts in the reaction chamber and associated conduits accommodates a wider pH range, as needed for certain biologically relevant PASADENA reagents.

2. The power supply is configured such that sufficient power and relatively wide pulses in the SOT sequence are provided; thereby rendering the polarizer function less sensitive to small changes in location and ambient magnetic fields.

3. Control is exercised over the chemistry of PASADENA, with mixing of reagents under nitrogen and better catalysis which results in a more reliable synthesis; thereby removing a source of variability between successive 'runs' of the polarizer.

4. The inventive apparatus is automated; thereby removing the need for multiple operators during a hyperpolarization experiment, easing the path to effective in vitro and in vivo experimentation.

Exemplary Process, System and Apparatus

In one aspect, the system and/apparatus of the subject matter includes a reaction chamber. In some embodiments, in addition to the reaction chamber, the system/apparatus further includes a coil surrounding the reaction chamber. In some embodiments, in addition to the reaction chamber, the system/apparatus further includes an electromagnet surrounding the coil for generating a static magnetic field. In some embodiments, in addition to the reaction chamber, the system/apparatus further includes a power source for supplying power to the coil and electromagnet. In some embodiments, in addition to the reaction chamber, the system/apparatus further includes a series of valves employed for fluid flow and delivery. In some embodiments, in addition to the reaction chamber, the system/apparatus further includes a central processor.

In another aspect, one or more reactants (e.g., one or more image reagent solutions; one or more catalysts; a gas containing/enriched in parahydrogen) are mixed and reacted in a reaction chamber. Additionally, radio frequency (R.F.) pulses are transmitted into the reaction chamber. In some embodiments, the transmission takes place after the completion of the hydrogenation reaction. In some embodiments, the transmission takes place during or concurrently with the hydrogenation reaction.

In some embodiments, an exemplary process further includes the steps of providing parahydrogen and for producing an image reagent solution comprising a catalyst.

In some embodiments, an exemplary process further includes providing transmitting R.F. pulses provided by a coil to enact a spin-order transfer sequence in the hyperpolarized product.

In some embodiments, an exemplary process further includes ejecting the hyperpolarized product from the reaction chamber.

In some embodiments, an exemplary process further includes filtering the hyperpolarized product to remove the catalyst.

In some embodiments, an exemplary process further includes introducing the filtered hyperpolarized product into a biological subject. Introduction of the hyperpolarized product into a biological subject can be achieved by injection, inhalation, ingestion, topical absorption, or by a combination of methods.

In some embodiments, the hyperpolarized product can be repeatedly introduced into the subject at a reasonable time interval to facilitate the imaging process. For example, the hyperpolarized product can be delivered twice or more, three times or more, four times or more, five times or more, six times or more, seven times or more, eight times or more, nine times or more, or ten times or more.

In some embodiments, an exemplary process further includes exposing the biological subject to a high-field nuclear magnetic resonance spectrometer.

One of skill in the art will understand that not all steps mentioned above need to be included in a process of hyperpolarization. In some embodiments, multiple steps in the process can occur at the same time. For example, the ejection of hyperpolarized product from the reaction chamber and filtration of the same product can take place as the same time when, for example, the outlet of the reaction chamber contains a built-in filter.

It will also be understood by one of skill in the art, that the same method step can take place multiple times to further improve efficiency. For example, r.f. can be introduced at multiple time intervals into the reaction mix. Similarly, filtration can also take place multiple times to ensure purity.

The systems and apparatuses of the subject matter are also broadly defined. For example, a system can include multiple apparatuses, in addition to any conventionally available equipments, apparatuses and/or material to perform the functions described herein. It will also be understood by one of skill in the art that, in some embodiments, one apparatus is provided that performs the functions described herein. In some embodiments, more than one apparatuses are used to perform the functions described herein.

Quality Assurance Procedures

A system (or apparatus) of the subject matter (e.g. a PASADENA polarizer) is unique in its ability to achieve an extremely high degree of hyperpolarization at liquid state temperatures within seconds all at a relatively low cost. This is achieved by catalytic addition of molecular parahydrogen to a precursor molecule, while spin order is manipulated consecutively for the generation of net polarization on a designated nucleus, in this case $^{13}C$. Nuclear spin polarization characterizes the alignment of spins exposed to a magnetic field, and corresponds to the fraction of all spins that contribute to NMR signal (Eq. 1):

$$P = \frac{N(\uparrow) - N(\downarrow)}{N(\uparrow) + N(\downarrow)} \qquad [\text{Eq. 1}]$$

At ambient temperature, the thermal energy exceeds the transition energy of the spin states by orders of magnitude, leaving only ~1-100 ppm of all spins contributing to the overall NMR signal. This is described mathematically by the Boltzmann distribution (Eq. 2):

$$P_{Boltzmann} = \tanh\left(\frac{\gamma \hbar B_0}{2k_B T}\right) \approx \frac{\gamma \hbar B_0}{2k_B T} \qquad [\text{Eq. 2}]$$

(where $\gamma$ is gyromagnetic ratio characteristic for a nucleus of interest, $\hbar$ is the Plank constant, $B_0$ is the field strength, $k_B$ is the Boltzmann constant and T is the temperature).

Hyperpolarization techniques hold the potential of increasing polarization to the order of unity, which is an enhancement of 4-5 orders of magnitude ($\eta_{observed}$) with respect to the thermal polarization originating from the magnetic field (Eq. 3):

$$\eta_{observed} = \frac{P_{HP}}{P_{Boltzmann}} \qquad [\text{Eq. 3}]$$

The polarization achieved in total, $P_{HP}$, provides a measure for the efficiency of the hyperpolarization technique, independent of the specific system for detection. It is predominantly used herein (Eq. 4):

$$P_{HP} = \eta_{observed} \cdot P_{Boltzman} \qquad [\text{Eq. 4}]$$

PASADENA hyperpolarization employs the spin order added to the precursor molecule by addition of parahydrogen to form spin polarization on a third, designated nucleus, such as, but not limited to, $^{13}C$ or $^{15}N$ [Kuhn L. T., and Bargon J. *Transfer of parahydrogen-induced hyperpolarization to heteronuclei*. Topics in current chemistry 276: (2007) 25-68].

The two spin ½ system of parahydrogen was predicted in 1924 by Born and Heisenberg [Born M., and Heisenberg W. *The quantum theory of molecules*. Annalen Der Physik 74: (1924) 1-31], and experimentally measured three years later by Bonhoeffer [Bonhoeffer K. F., and Harteck P. *Experiments on para-hydrogen and ortho-hydrogen*. Naturwissenschaften 17: (1929) 182-182]. The singlet state holds spin zero (Eq. 5), while the triplet states has spin one (Eq. 6).

$$|0,0\rangle = 1/\sqrt{2}(|\uparrow\downarrow\rangle - |\uparrow\downarrow\rangle) \qquad [\text{Eq. 5}]$$

$$|1,1\rangle_1 = |\uparrow\uparrow\rangle$$

$$|1,-1\rangle_2 = |\downarrow\downarrow\rangle$$

$$|1,0\rangle_3 = 1/\sqrt{2}(|\uparrow\downarrow\rangle + |\uparrow\downarrow\rangle) \qquad [\text{Eq. 6}]$$

The R.F. pulse sequence to form scalar order in the $^{13}C$ nucleus in a parahydrogenated molecule is described in Goldman et al. [M. Goldman, and H. Johannesson, *Conversion of a proton pair para order into C-13 polarization by r.f. irradiation, for use in MRI*. Comptes Rendus Physique 6 (2005) 575-581]. Since the evolution of the spin system is affected by the J couplings characteristic to the molecular environment (FIG. 11), the spin order transfer sequence is specific to each individual molecule.

The method has previously been restricted, as early examples were non-biological molecules, soluble only in acetone. A water-soluble molecule which was toxic at the doses employed, and confined to the vasculature after injection in vivo was employed in a demonstration of $^{13}C$ angiography [K. Golman, et al., *Parahydrogen-induced polarization in imaging: Subsecond C-13 angiography*. Magnetic Resonance in Medicine 46 (2001) 1-5; Mansson S. et al., *C-13 imaging—a new diagnostic platform*. European Radiology 16: (2006) 57-67]. A metabolizable molecule, $^{13}C$ sodium maleate which is converted to $^{13}C$ succinate by two hydrogenation steps, has also been reported from this laboratory. In a recent report, we described hyperpolarization of $1-^{13}C$ in succinate [Bhattacharya P. et al., *Towards hyperpolarized 13C-succinate imaging of brain cancer*. J Magn Reson, 186: (2007) 108-113; Chekmenev E. et al., *PASADENA Hyperpolarization of Succinic Acid for MRI and MRS*. Journal of the American Chemical Society 130: (2008) 4212-4213]. Succinate is an intermediate in the tricarboxylic acid cycle and other significant metabolic pathways, including gluconeogenesis [Esteban M. A., and Maxwell P. H. *HIF, a missing link between metabolism and cancer*. Nature Medicine 11: (2005) 1047-1048; Rustin P., Munnich A., and Rotig A. *Succinate dehydrogenase and human diseases: new insights into a well-known enzyme*. European Journal of Human Genetics 10: (2002) 289-291].

With the advent of imaging reagents with the potential to broaden the use of parahydrogen hyperpolarization in biology, as described above in the subject matter apparatus, comes the need to standardize and automate equipment for this purpose. The following disclosure for the setup and optimization of polarized yield describes in more detail, quality assurance procedures necessary to achieve high levels of $^{13}$C hyperpolarization on a consistent basis.

In some embodiments, PASADENA is realized in three steps (FIG. 8), which determine the overall success of hyperpolarization. First, as source of the spin order, the quality of parahydrogen limits the level of hyperpolarization. Methods for parahydrogen generation are standard and not further discussed herein. Second, is the addition of parahydrogen to the $^{13}$C-enriched indicator molecule. Proper chemistry (catalyst) and reaction conditions (hardware) determine whether or not the target molecule is formed efficiently, in such a way that parahydrogen spin order is available for the third step, which entails the manipulations of the spins and transfer of polarization to $^{13}$C ($^{15}$N). Immediately after the hydrogenation reaction, R.F. pulses are applied to form polarization on the designated nucleus in the molecule. Hydrogenation and manipulation of spins by R.F. pulses are carried out within a confined space of a reactor vessel. The reactor vessel is surrounded by coils which provide a static low magnetic field ($B_0$ coil) and the designed and evolving excitation r.f. pulses ($B_1$ coil). Design and implementation of low field NMR manipulation is determined by the accuracy with which the quantum mechanical properties of the target molecule (J couplings) is known, and how well the designed manipulations are applied to the spins by R.F. hardware. Presently, the same sequence was used for two $^{13}$C molecules of interest. The highly reproducible operation of the PASADENA polarizer and use of 1-$^{13}$C Succinate-$d_{2,3}$, in vitro, described below, demonstrates application in a biological model.

Several of the key metabolites in the urea and choline cycles and neurotransmitter glutamine-glutamate, pathway can be detected and defined by Magnetic Resonance Spectroscopy (MRS) and can be the clinical drivers to $^{15}$N hyperpolarization. Hyperpolarizing the metabolites in these cycles can provide invaluable real time biochemical information about the molecular basis of diseases like cancer. For example, choline, synthesized in liver or taken in the diet, enters the brain from systemic circulation via a saturable transport at the blood brain barrier (BBB). The rate of uptake is proportional to blood choline concentration. Once across the BBB, choline enters neurons or glia via active transport. The majority of cellular choline is phosphorylated by choline kinase (CK) and its product phosphoryl choline (PC) is quantitatively the most important metabolite. The rate-regulatory step in choline metabolism is phosphorylcholine conversion to CDP-choline. In normal brain and in glioma, there will be rapid uptake of rapidly infused $^{15}$N hyperpolarized choline across the intact BBB, entry into cells and further conversion of choline to phosphorylcholine, via choline kinase. Intracellular accumulation of $^{15}$N choline and $^{15}$N PC could each reach 0.15 mM in the normal brain after 10 minutes. While free choline, PC and CDP-choline are not distinguishable by PET, the excessive uptake and metabolism of choline will yield signals of significantly different chemical shift in PASADENA/DNP CSI of $^{15}$N intermediates.

NMR receptivity scales as $\gamma^3$ for spin ½ nuclei. Therefore, direct NMR detection of low g nuclei results in lower signal-to-noise ratio compared to proton detection. As a result, even hyperpolarized $^{15}$N spins are inherently $(\gamma_{1H}/\gamma_{15N})^2 \sim 100$ fold less sensitive compared to hyperpolarized protons. While protons are better nuclei for detection, short spin lattice relaxation times prevent direct $^1$H hyperpolarized MR in biomedical applications.

Figure 19:
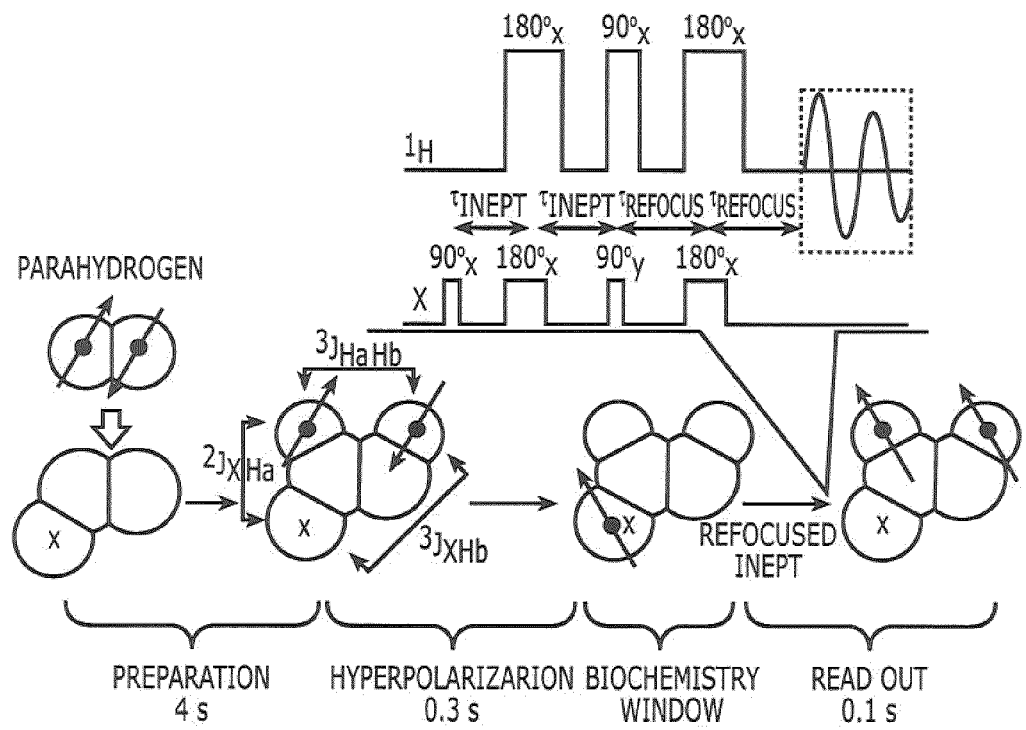
FIG. 19. A diagram, of molecular cis addition of parahydrogen followed by hyperpolarization of X nucleus ($^{13}C$ or $^{15}N$), polarization storage on X nucleus (potentially allowing monitoring of biochemical events on the time scale of minutes) followed by polarization transfer back to more sensitive protons for NMR detection.

The present subject matter demonstrates the utility of $^{13}$C for spin storage of hyperpolarization followed by $^1$H detection using Insensitive Nuclei Enhanced by Polarization Transfer (INEPT) polarization transfer sequence, which theoretically can provide up to ~(g1H/gX) 2 gain in sensitivity in hyperpolarized biomedical MR (FIG. 19). Specifically, the present subject matter hyperpolarized the $^{13}$C site of two well studied molecules, 1-$^{13}$C-succinate-$d_2$ and 2,2,3,3-tetrafluoropropyl 1-$^{13}$C-propionate-$d_3$ (TFPP), by PASADENA. Hyperpolarized succinate can be potentially exploited as a metabolic biomarker of cancer, while hyperpolarized TFPP has been shown to be a specific binder to lipids with a unique chemical shift signature in the lipid bound state potentially useful for plaque and cancer imaging.

The efficiency of the polarization transfer from $^{13}$C to $^1$H, demonstrated in as 41% (Example 4) for 1-$^{13}$C-succinate-$d_2$ and 50% for TFPP, is a ratio between the polarization detected after the transfer and $^{13}$C polarization as measured by a 12° excitation pulse before the INEPT transfer. While the efficiency of the polarization transfer was 50% or below, hyperpolarized protons are inherently 15.8 fold more sensitive compared to hyperpolarized $^{13}$C. As a result, proton detection of hyperpolarized 1-$^{13}$C-succinate-$d_2$ and TFPP increased the overall sensitivity by a factor of 6.5 and 7.9, respectively.

Figure 21:
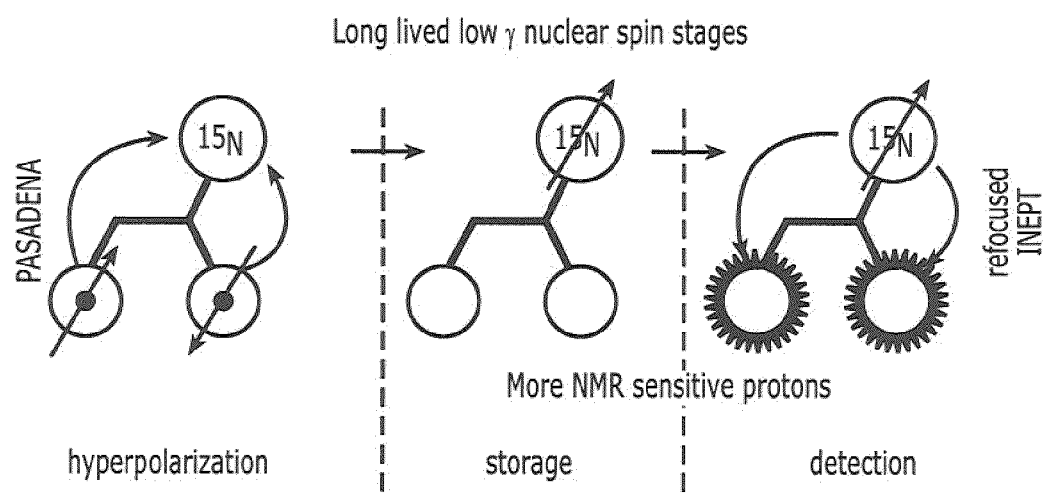
FIG. 21. Diagram of method towards hyperpolarized proton MR using $^{15}N$ as a spin storage of hyperpolarization.

More importantly, using this approach (FIG. 21), hyperpolarized $^{15}$N MR would become an attractive biomedical and potentially clinical tool due to the much longer spin lattice relaxation time 464 s owing to low γ, but now with the added advantage of more sensitive detection using proton NMR (γ215N≈γ21H/100). In addition, we estimate that $^{15}$N hyperpolarization in choline group can be transferred to the nine methyl protons thereby nine spins would be hyperpolarized compared to one $^{15}$N per molecule. This could additionally increase the detection sensitivity by factor of nine resulting in overall theoretical signal gain of up to 900 compared to direct detection of hyperpolarized $^{15}$N. Furthermore, proton imaging, localized spectroscopy and chemical shift imaging (CSI) will allow improved spatial resolution by g1H/gX in each dimension at a given gradient strength.

Specific advantages of $^{15}$N NMR can now be exploited by hyperpolarization in the understanding of urea cycle, glutamine-glutamate and choline metabolism in vivo. Furthermore, hyperpolarized $^{15}$N NMR can have utilized for structure elucidation of proteins and oligonucleotides. Accordingly, the present subject matter shows that: 1)$^{15}$N Hyperpolarized MRI and MRS are appealing and feasible; 2) Major advances in SNR and time for imaging has been achieved; 3) Luxury of time: Metabolite flux measurements for 30 minutes or more can be accomplished; and 4) Spin storage: Broadens the approach in case of no nitrogen channel in MR scanners as well as in hyperpolarized conventional $^1$H MR.

Table 1 provides the overall quality assurance methods disclosed in the present subject matter for PASADENA hyperpolarization. For convenience, the materials prerequisite (column A) are describe in "Prerequisites for PASADENA," while installation, calibration (column B) and operation of the polarizer (column C) are presented in "Methods for PASADENA."

1. Prerequisites for PASADENA:
Parahydrogen

Commercially available ultra pure hydrogen (Gilmore, South El Monte, USA) was catalytically converted to parahydrogen (pH2) by slow passage over granular hydrous ferric oxide (IONEX-type O-P catalyst; Molecular Products Inc., Lafayette, Colo., USA). After the gas was converted to parahydrogen it was stored in 7 L aluminum cylinders at room temperature at a pressure of 33 bar. The quality of pH$_2$ was determined to be >97% by high resolution NMR [P. Bhattacharya et al., *Ultra-fast three dimensional imaging of hyper-* polarized C-13 in vivo. Magnetic Resonance Materials in Physics Biology and Medicine 18: (2005) 245-256]. Each batch was used within seven days, with no measurable decrease in the yield.

Imaging Product Precursors

For initial calibration, a previously validated PASADENA reagent, $^{13}$C HEA, was prepared as an aqueous solution. 2-5 mg HEA (Isotec, Sigma Aldrich, USA) were dissolved in a small volume of phosphate buffer, pH 7.0, and mixed with the catalyst solution and de-aerated. For further calibration and biomedical studies, 1-$^{13}$C-fumaric acid-d$_{2,3}$ (1-$^{13}$C-FUM-d$_{2,3}$); (Cambridge Isotope Laboratories, Andover, Mass., USA) was dissolved in a small volume of phosphate buffer at pH=2.9. Low pH was necessary for the accurate determination of couplings in the resulting hydrogenation product, 1-$^{13}$C succinate (as described further below). The imaging reagent solution was added to the catalyst and alternately exposed to inert gas (N$_2$) and vacuum. The resulting mixture contained 1-3 mmol/L 1-$^{13}$C-FUM-d$_{2,3}$ and 2.0-2.5 mmol/L catalyst concentrations in 50 mmol/L pH=2.9 phosphate buffer. The aqueous mixture of catalyst and molecular precursor was prepared fresh, prior to each hyperpolarization procedure.

Hydrogenation Catalyst

In some embodiments, a bisphosphine ligand, 1,4-bis-[(phenyl-3-propane sulfonate)phosphine]butane disodium salt (Q36333, Isotec, OH, USA), was dissolved in H$_2$O/D$_2$O to yield 2.5-3.0 mmol/L concentration followed by removal of oxygen using vacuum and nitrogen connected via a manifold. The rhodium catalytic moiety was then introduced to the reaction mixture under N$_2$ atmosphere as a solution of bis (norbornadiene)rhodium (I) tetrafluoroborate (catalog number 45-0230, CAS 36620-11-8, Strem Chemicals, Mass. USA) in acetone with 5% molar excess of bisphosphine ligand with respect to rhodium. The resulting solution was vigorously shaken and acetone was removed under vacuum. Excess of biophosphine is necessary for complete removal of rhodium. The imaging reagent solution was added to the catalyst and alternately exposed to inert gas (N$_2$) and vacuum. The resulting mixture contained 1-3 mmol/L FUM and 2.0-2.5 mmol/L catalyst concentrations in 50 mmol/L pH 2.9 phosphate buffer. The aqueous mixture of catalyst and molecular precursor was prepared fresh, prior to each hyperpolarization procedure.

The completed PASADENA solution of precursor and catalyst was drawn into a 20 mL plastic syringe and connected to valve 2 of the PASADENA polarizer (FIG. 5), for injection of the desired amount of imaging reagent precursor for each experiment (3.5 mL unless otherwise noted). When prepared in these proportions, hydrogenation of the precursor was carried to completion and no residual precursor (HEA or 1-$^{13}$C FUM) was detected by $^{13}$C NMR.

In some embodiments, transition metal catalysts are used as catalysts to activate H$_2$ for performing hydrogenation catalysis. In some embodiments, non-metal based catalysts are used. Catalysts of the embodiments function via numerous mechanisms. For example, first, via oxidative addition: the most common method of activating H$_2$ on a metal with d electrons (d$^2$ or higher). Metal center typically needs to have an empty coordination site in order to bind the H$_2$ first, prior to the oxidative addition. Second, via hydrogenolysis: the only way that early transition metals with d$^0$ counts can activate H$_2$. Lanthanides and actinides also typically use hydrogenolysis. As with oxidative addition, the metal center needs to have an empty orbital to bind the H$_2$ and an anionic ligand (e.g., alkyl, halide) that can be protonated off. No change in oxidation state of the metal. Third, via heterolytic cleavage: in many ways quite similar to hydrogenolysis except that the proton produced does not directly react with an anionic ligand coordinated to the metal, but rather with an external base that typically has to transfer it back to the metal center to complete the catalytic cycle. For example, Ruthenium (e.g., Ru$^{+2}$) is the most common metal that uses heterolytic cleavage as a mechanism. No change in oxidation state of the metal is resulted.

Exemplary hydrogenation catalysts include but are not limited to tyrosine; N-phenyl-anthranilic acid; fullerene; fluorescein; rhodamine B; rhodium or a rhodium-based compound chlorotris-(triphenylphosphine)-rhodium(I)/RhCl (PPh$_3$)$_3$); platinum or a platinum-based compound; palladium or a palladium-based compound; ruthenium or a ruthenium-based compound; Lanthanide-based catalyst (e.g., Cp*$_2$LuH)$_2$; iridium-based catalyst (e.g., a complex of iridium with 1,5-cyclooctadiene, tris-cyclohexylphosphine, and pyridine); tert-butanol; potassium tert-butoxide; or a combination thereof. One of skill in the art will understand that any hydrogenation catalysts known in the art can be used in reactions of the subject matter.

Determination of J-Couplings of the PASADENA Agents

Figure 8A:
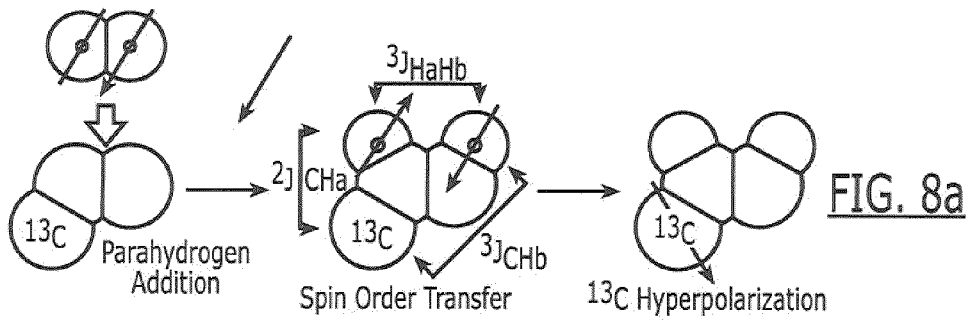
FIG. 8a. A diagram representing the chemistry of PASADENA.
Figure 8B:
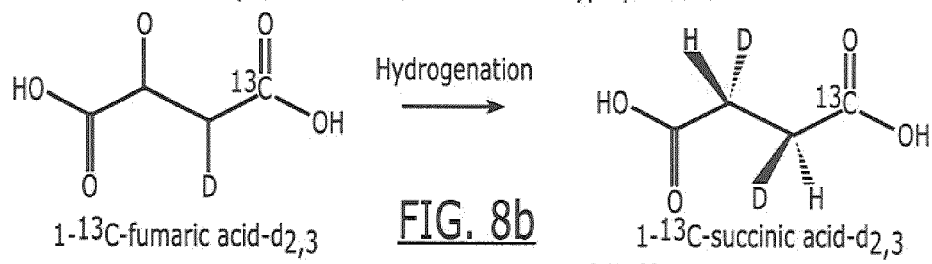
FIG. 8b. A diagram representing hydrogenation in the chemistry of PASADENA.
Figure 8C:
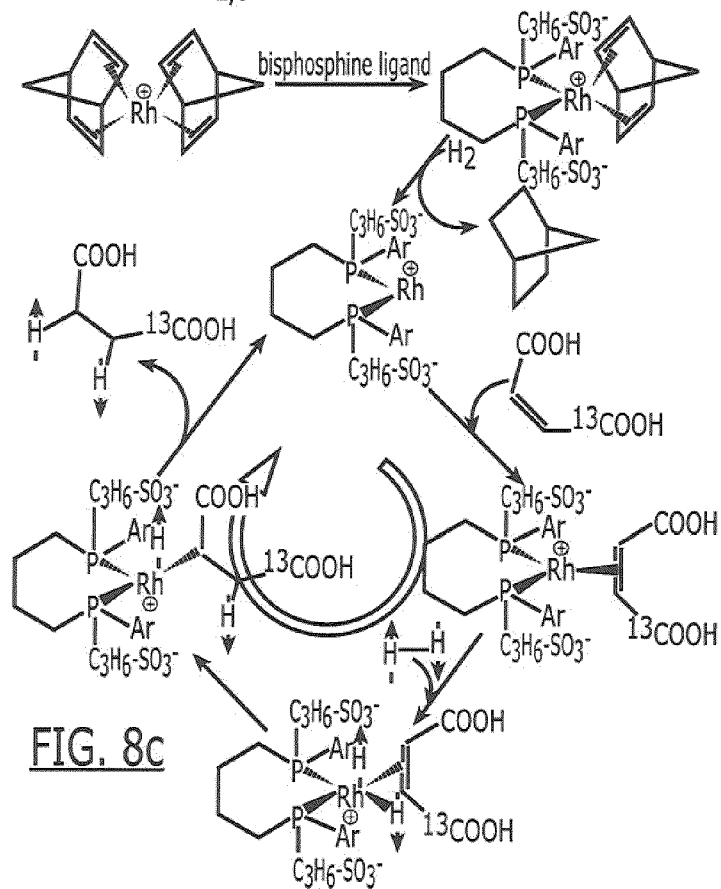
FIG. 8c. A diagram representing the hydrogenation reaction cycle of Rhodium based catalyst.

As indicated in FIG. 8, and described in some detail by Bowers [Bowers C R, Weitekamp D. *Transformation of Symmetrization Order to Nuclear-Spin Magnetization by Chemical-Reaction and Nuclear-Magnetic-Resonance*. Phys Rev Lett, 57(21): (1986) 2645-2648], Bargon [Natterer J, Bargon J. *Parahydrogen induced polarization*. Progress in nuclear magnetic resonance spectroscopy 31. 1997: Part 4: 293-315] and more recently by Goldman et al. [M. Goldman et al. *Hyperpolarization of C-13 through order transfer from parahydrogen: A new contrast agent for MRI*. Magnetic Resonance Imaging 23 (2005) 153-157; M. Goldman, and H. Johannesson, *Conversion of a proton pair para order into C-13 polarization by r.f. irradiation, for use in MRI*. Comptes Rendus Physique 6 (2005) 575-581], significant transfer of polarization from parahydrogen to the third nucleus is achieved through design and implementation of a spin transfer sequence which is then applied to the mixture of $^{13}$C reagent and rhodium catalyst described previously (Imaging Product Precursors). In order to form $^{13}$C hyperpolarization by R.F. radiation, the spin order transfer ("SOT") sequence should be tailored to the J-couplings of the parahydrogen and the nucleus to-be-polarized ($^2J_{CHa}$, $^2J_{CHB}$, $^3J_{HaHb}$).

Quantification of Hyperpolarization

A number of strategies have been employed to quantify the extent of hyperpolarization [Association N.E.M. *Determination of signal-to-noise ratio (SNR) in diagnostic magnetic resonance imaging*. NEMA Standards, Publication MS 1-2001 (2001)]. In the present application, the following convention was applied. The signal enhancement ($\eta_{observed}$) achieved by hyperpolarization was quantified in respect to the signal of a thermally polarized sample (100% ethanol, 188 mM of natural abundance $^{13}$C at each site (Eq. 7)). The signal intensities were determined by numerical integration (xWIN-NMR software, Bruker Biospin, Germany)

$$\eta_{observed} = \frac{P_{HP}}{P_{Boltzmann}} = \frac{I_{HP}}{I_{ref}} \cdot \frac{C_{ref}}{C_{HP}} \qquad [\text{Eq. 7}]$$

(where $I_{HP}$, $I_{ref}$, $C_{HP}$ and $C_{ref}$ are integral intensities and molar concentrations of hyperpolarized and reference samples, respectively).

T1 Decay of Hyperpolarization

Figure 15:
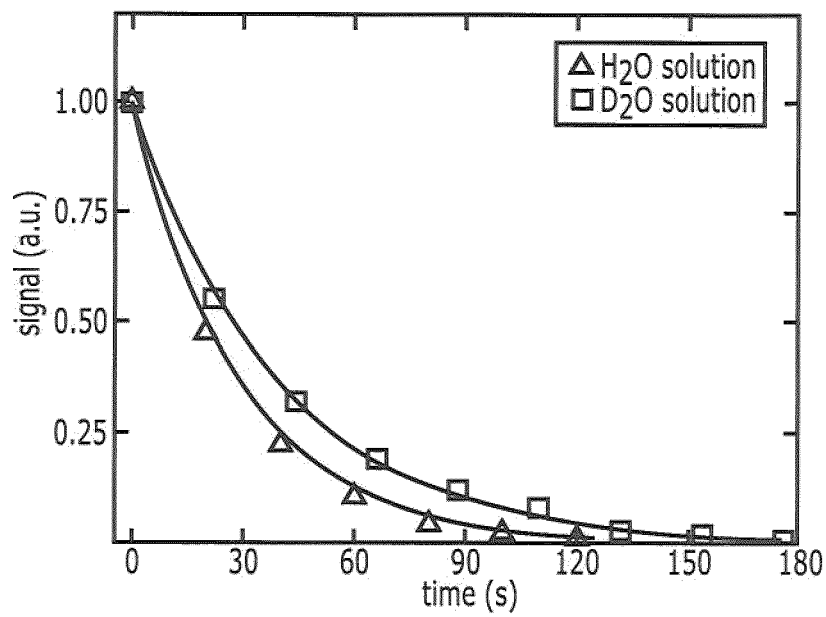
FIG. 15. A graph of the $T_1$ measurement of hyperpolarized 1-$^{13}C$-succinate-$d_{2,3}$ in $D_2O$ ($T_1$=[40±2] s) and in $H_2O$ ($T_1$=[27±3] s)

The decay of $^{13}$C polarization caused by longitudinal relaxation ($T_1$) of the hyperpolarized sample during the delivery to the detection system was determined (FIG. 15). This allows for the determination of the nascent signal enhancement (Eq. 8), and nascent level of achieved polarization (Eq. 9).

$$\eta^{t=0} = \eta_{observed} \cdot \exp\left(-\frac{\text{delivery time}}{T_1}\right) \quad [\text{Eq. 8}]$$

$$P_{HP}^{t=0} = \eta^{t=0} \cdot P_{Boltzmann} \quad [\text{Eq. 9}]$$

Unless otherwise indicated, $P_{HP}^{t=0}$ and $\eta^{t=0}$ are reported in the work presented, using a $^{13}$C polarization of $P_{Boltzman}=0.00041\%$ or 4.1 ppm at 298K and 4.7 T. T1 values for the PASADENA reagent concerned in calibration and quality assurance ("QA") were determined directly. A series of small angle ($\alpha \approx 8°$) FID experiments was employed to probe the decay of the magnetization of the hyperpolarized agents (small excitation angle approximation, SEA). The T1 values were extracted by the fit of Equation 10 (Eq. 10) to the data points, taking into account the loss of magnetization caused by the excitation pulses.

$$I(t) = I_0 \cdot e^{-\left(\frac{t}{T_1}\right)} \cdot e^{-\left(\frac{1-\cos(\alpha)t}{TR}\right)} \quad [\text{Eq. 10}]$$

2. Methods for PASADENA

In some embodiments, the subject matter method for set-up and calibration of the PASADENA polarizer comprises of seven steps. Together these constitute the quality assurance method which ensures maximum hyperpolarization and optimal reproducibility for each PASADENA reagent.

Step 1. Polarizer Fluid Control System

An automated fluid control system delivers reagents to the reaction chamber. The steps of the hyperpolarization experiment, including the fluid control system were controlled by custom software (LabView platform, National Instruments, Austin, Tex., USA), able to load a R.F. pulse file, and to store the sequence of timings and events in a separate file. The following procedure was optimized to produce hyperpolarized agents in less than one minute, including: (i) Flush the system with $N_2$ gas (14 bar, valves 3, 4, 5 open), (ii) load the aqueous solution of precursor and catalyst in the $N_2$ path (valve 2 open) (iii) fill the previously flushed reactor with 10 bar $pH_2$ and pressurize $N_2$ path (valves 1 and 3 open), (iv) close $pH_2$ path, inject precursor solution in $pH_2$ atmosphere (valves 3 and 4 open) while applying $^1H$ R.F. saturation pulses (to keep the hydrogen in the singlet state), (v) apply the spin order transfer sequence, and (vi) deliver the hyperpolarized solution to the detector (e.g., small animal NMR or clinical MRI scanner) employing residual pressure (valve 5 open).

Step 2. Calibration of the NMR System of the Polarizer

An initial calibration of the NMR system of the polarizer is necessary to perform accurate R.F. manipulations on the spins of the PASADENA agent in the reactor. Since the R.F. electronics and coil were designed for transmission only, a second, external high-field NMR system was employed for the detection (7 T Mercury spectrometer, Varian, Palo Alto, USA). A sample of saturated 1-$^{13}$C sodium acetate $CH_3$-$^{13}$COONa in $D_2O$ was pre-polarized at high field for 3 minutes, delivered to the polarizer for a $^{13}$C inversion pulse of arbitrary length, followed by delivery back to the high field unit, where the resulting magnetization was detected by a 90° pulse-acquisition.

Step 3. Determine Center Frequency of NMR System of Polarizer

To center the frequency, a $^{13}$C sample was subjected repeatedly to a "pulse$_{polarizer}$-delay-pulse-acquisition$_{Varian}$." experiment while the strength of the low-field in the polarizer was incremented by 0.1 mT, and the R.F. was kept constant. The optimal field for the 18 kHz carbon pulse was found to be ~0.76 mT at the position of the Hall sensor of the Gauss meter. Once the optimum field for the carbon frequency was found, the corresponding proton frequency was calculated (75 kHz).

Step 4. Thermal Flip Angle Calibration

Figure 9:
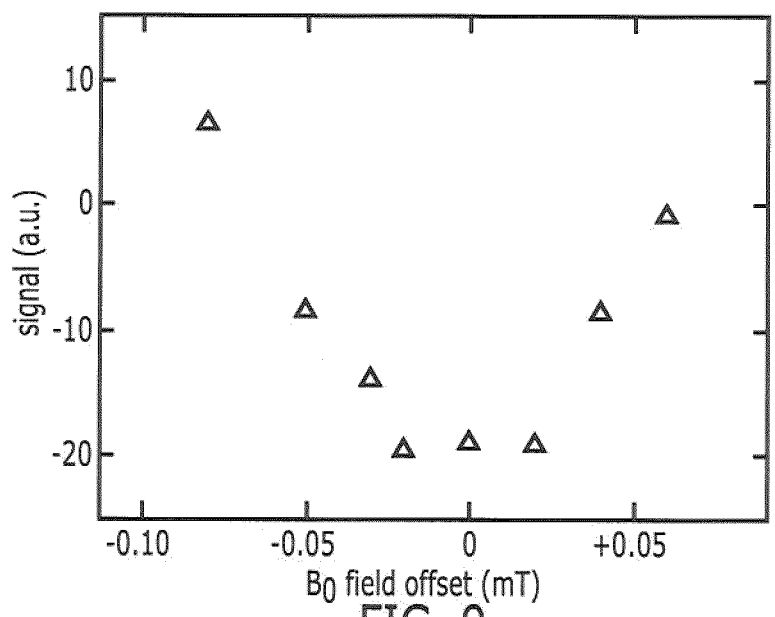
FIG. 9. A graph of the data collected to center the frequency of the low field MR-unit of the polarizer.
Figure 10:
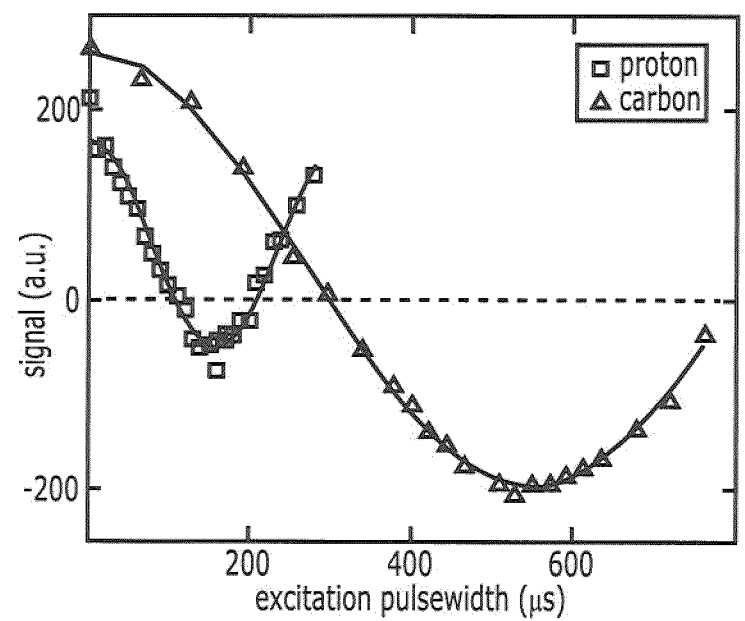
FIG. 10. A graph of the date collected for $^{13}C$ and $^1H$ flip angle calibration of the low field MR unit in the polarizer.

For the calibration of the flip angles of the R.F. excitation pulses ($B_1$), the previous protocol for the combination of low-field inversion pulse and high field detection (FIG. 9) was employed. At constant $B_0$, the width of the R.F. pulse given in the polarizer was varied for $^{13}$C and $^1H$ frequencies independently. The acquired data was fitted using a $T_1$ corrected cosine function, providing an estimate for the $B_1$ fields. The center frequencies of proton and carbon have been aligned in FIG. 10 (left). The uncorrected frequencies, or 'true' data, are shown in FIG. 10 (right).

Step 5. Determination of J-Couplings

While the J-coupling constants for HEP employed in calibration of the polarizer, have previously been reported [M. Goldman, and H. Johannesson, *Conversion of a proton pair para order into C-13 polarization by r.f. irradiation, for use in MRI*. Comptes Rendus Physique 6 (2005) 575-581], the relevant J-couplings for succinate were unknown and were determined by computations employing GAMMA simulations [Smith S. A. et al., *Computer-Simulations in Magnetic-Resonance—an Object-Oriented Programming Approach*. Journal of Magnetic Resonance Series A 106: (1994) 75-105] and confirmed by experiment [Chekmenev E. et al., *PASADENA Hyperpolarization of Succinic Acid, for MRI and MRS*. Journal of the American Chemical Society 130: (2008) 4212-4213]. The $^{13}$C spectra (FIG. 11) was acquired using a saturated (100 mM) aqueous solution of succinic acid (natural abundance, Isotec, Sigma Aldrich, USA) with a 14 T high resolution spectrometer (Varian, H/C/N probe, 256 acquisitions) without decoupling.

Figure 11A:
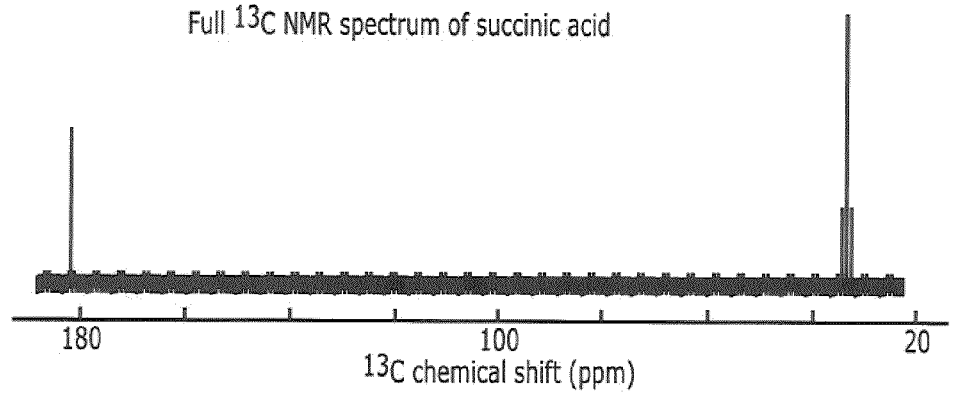
FIG. 11a. A $^{13}C$ NMR spectrum of natural abundance succinic acid at pH 7.4.
Figure 11B:
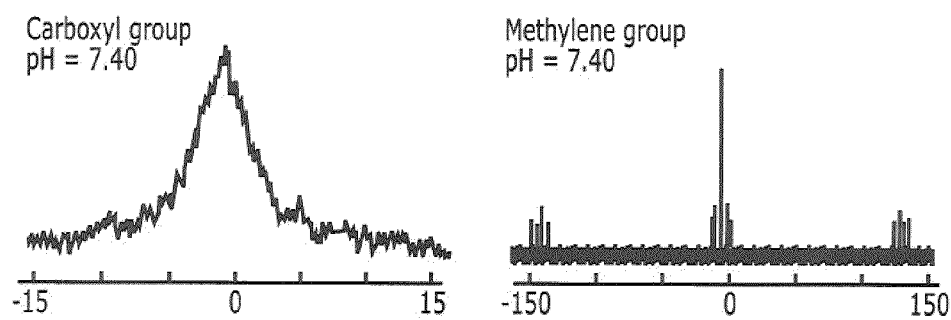
FIG. 11b. A $^{13}C$ NMR spectra of carboxyl (1,4-$^{13}C$, ~185 ppm) and methylene (2,3-$^{13}C$, ~35 ppm) groups at pH 7.4.
Figure 11C:
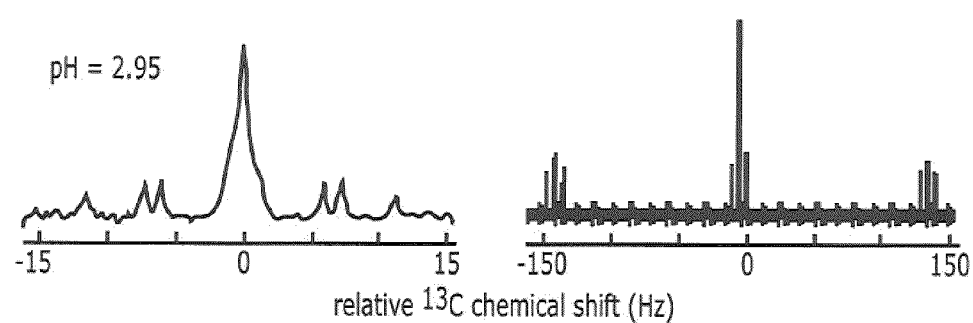
FIG. 11c. Simulations and measured $^{13}C$ NMR spectra of carboxyl and methylene groups at pH 2.95.

At pH 7.4, substantial line broadening, attributed to chemical proton exchange, was observed on the carboxyl group (~185 ppm) which prohibited the resolution of line splitting by J-couplings. All experiments were therefore performed at pH 2.95<<pKa (FIG. 11).

For the simulations, the spectra of a $^{13}$C spin coupled to two protons (C, Ha, Hb) was calculated under the effect of Zeemann interaction and indirect couplings ($^2J_{CHa}$, $^2J_{CHb}$, $^3J_{HaHb}$). The simulations were performed iteratively varying the J-couplings until the corresponding experimental spectra (Levenberg-Marquart least-square fit) was found ($^2J_{CHa}$=−7.15 Hz, $^3J_{CHb}$=5.82 Hz and $^3J_{HaHb}$=7.41 Hz).

These constants were programmed for the polarizer and employed to tailor the spin order transfer sequence to the target molecule, 1-$^{13}$C succinate-d2,3, during subsequent calibrations.

Figure 12:
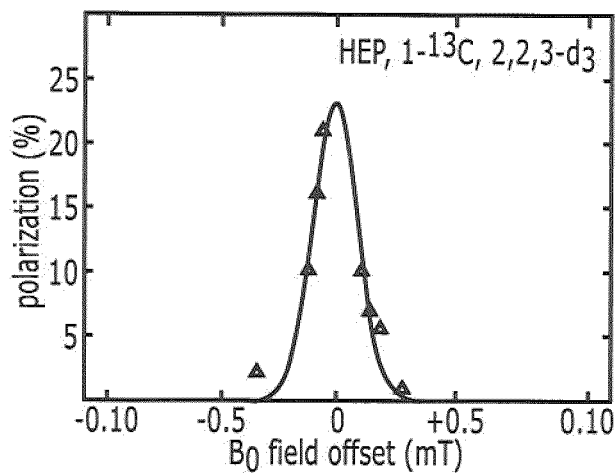
FIG. 12. A graph of the data collected for calibration of the center frequency of the low field MR unit.

Step 6. Optimization of Spin Order Transfer: $B_0$ Calibration with Hyperpolarization Introducing parahydrogen and substituting a PASADENA reagent and catalyst (Section A—Prerequisites for PASADENA) in place of $^{13}$C acetate used for calibration, acceptable levels of hyperpolarized signal were achieved as detected in the high-field spectrometer. The optimization of $B_0$ to center the frequency was repeated over a smaller range, recording the yield of hyperpolarization at each field. Maximal polarization of P=21% (nominal $^{13}$C signal enhancement ≃150,000) was found at 1.736 mT (FIG. 12 left). Polarizer "efficiency" may be assumed "optimum" after the preceding 6 quality assurance steps.

As expected, hyperpolarization was extremely sensitive to deviations from the precise low magnetic field applied during spin order transfer. At +/−0.009 mT from the optimal field, the polarization declined by 50% (FWHM=0.018 mT) (FIG. 12 right). Marked variations persisted in the polarization yield at the same field strength (FIG. 13 left), which were attributed to remaining variables in R.F. amplifier performance, reagent preparation technique and, because signal decays rapidly before detection, to prolonged and variable sample delivery times to the spectrometer. Delivering hyperpolarized sample and triggered detection in the NMR scanner were further optimized. The polarizer was moved to the in vivo suite, where it was positioned carefully 7.63 m±0.5 cm from a small-animal horizontal bore, high field MRI (4.7 T Bruker MRI scanner). An automated system was implemented, whereby the hyperpolarized solution was driven by remaining gas pressure in the reactor, through polyethelene (PE) tubing from the polarizer to an NMR-tube in a dual-tuned $^1$H/$^{13}$C solenoid coil in the MR scanner; where after a precise interval (33 seconds) acquisition was triggered. The solution was then drained to permit successive experiments without coil repositioning. Together, these measures proved to be essential for the reliability of the level of achieved polarization, as quantified later. The modifications implemented improved the stability of the $B_0$ and provided stronger $B_1$, allowing for better R.F. performance and less sensitivity of hyperpolarization of HEP to off-resonant $B_0$, as demonstrated in FIG. 13 (left).

Figure 13A:
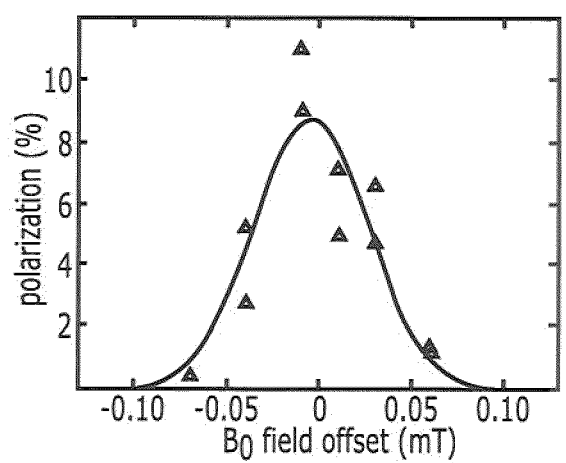
FIGS. 13a-b. Graphs of the data collected for center frequency of the low field MR unit.
Figure 13B:
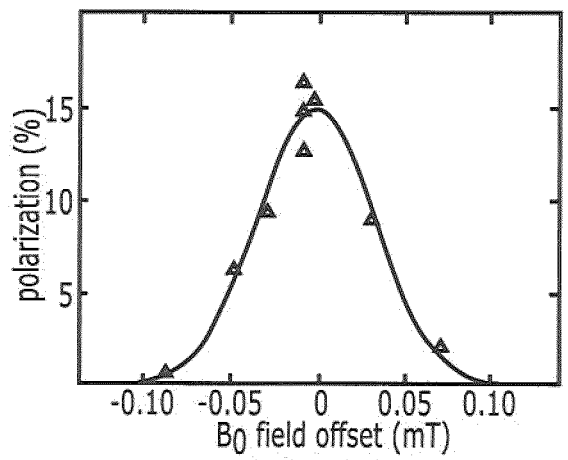
Figure 14A:
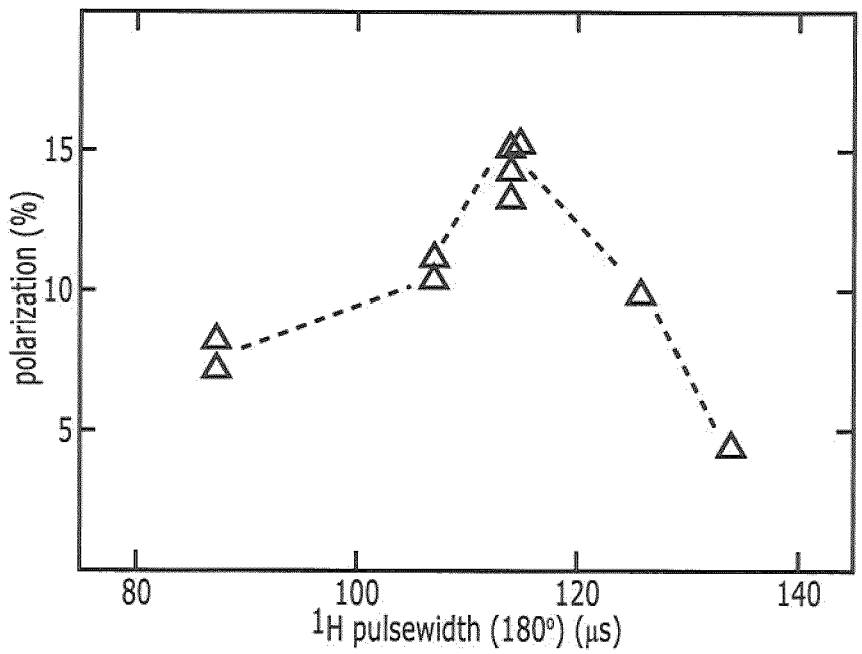
FIG. 14. Graphs of the data collected for optimization of SUC hyperpolarization yield by two-dimensional optimization of the $B_1$ flip angles.
Figure 14B:
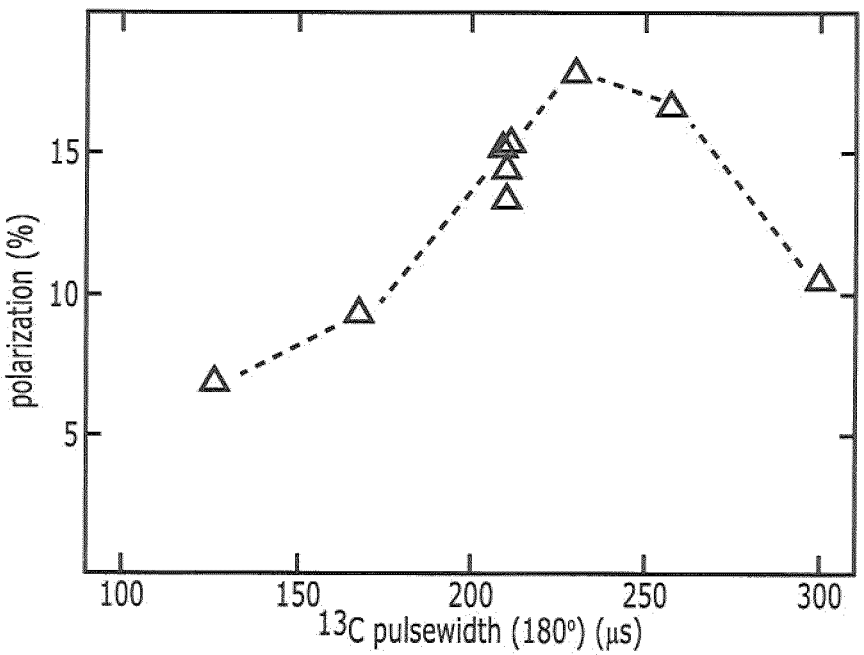
Figure 14C:
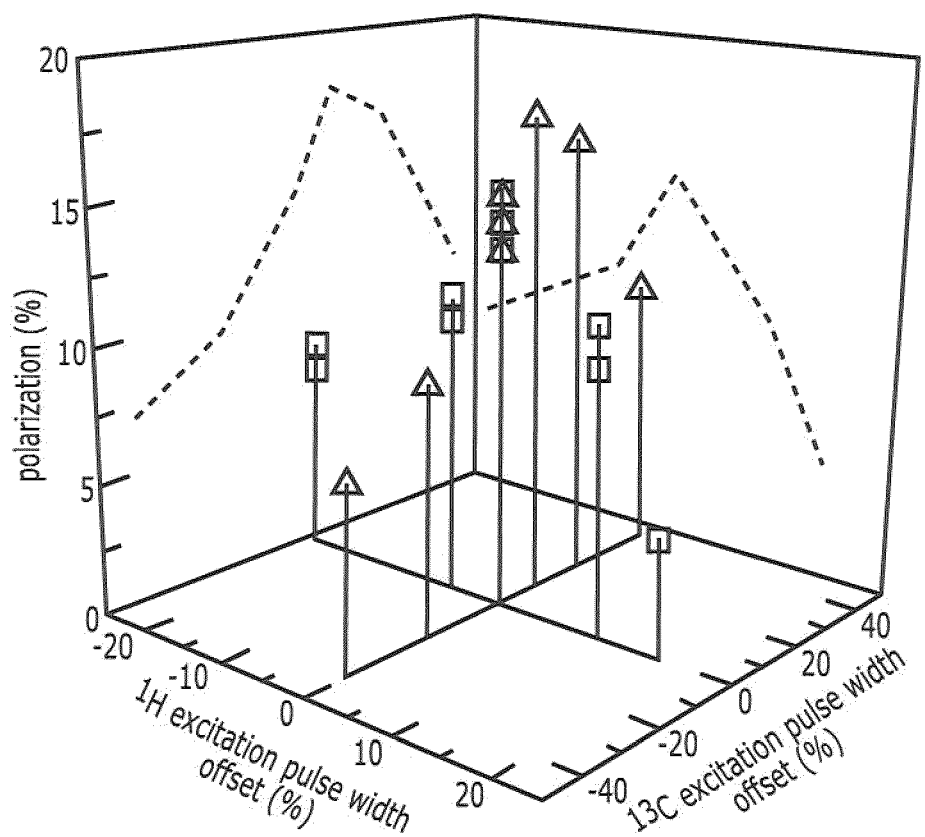

Step 7. B1 Optimization with Hyperpolarization:

With the goal of in vivo application, the next group of calibrations were performed with the non-toxic water soluble PASADENA biomolecule SUC (FIG. 13, right). The hyperpolarization yield was incrementally increased by further optimization of the individual pulse widths of $^{13}$C, $^1$H in the SOT sequence, at constant $B_0$ (FIG. 14). First, the pulse width of the $^1$H pulses in the SOT was varied (FIG. 14a). The optimum was determined to be at 115 μs (50 V). Next, keeping the $^1$H pulse width constant, the experiment was repeated while varying the $^{13}$C pulse widths in the SOT sequence (FIG. 14b). Each experiment was conducted eight times. The optimum $^{13}$C pulse width was 230 μs (25 V). FIG. 14c demonstrates the multidimensional character of this optimization. The maximal polarization achieved with 1-$^{13}$C succinate under these conditions was 18%.

Based on the exemplary quality assurance steps, two important properties were defined of PASADENA for a biologically appropriate molecular imaging reagent in vitro. First, $T_1$ of hyperpolarized MRI signal was shown to be critical in defining duration of enhanced $^{13}$C (or $^{15}$N) MRI signal after delivery. The maximum polarization achieved in PASADENA was also determined as relevant for quantitative comparison with competing reagents and hyperpolarization techniques. Secondly, the effect of $D_2O$ prolonging the lifetime of polarization was shown to be a general property, and of value for most hyperpolarization techniques. The $T_1$ decay time for HEP was 70 s in $D_2O$, as compared to 50 s in $H_2O$ (pH 7, $B_0$=4.7 T).

The relaxation constant of hyperpolarized 1-$^{13}$C-succinate-d2,3 was determined to be $T_1$=[27±3] s (N=3, pH 3, $B_0$=4.7 T) in $H_2O$ solvent (at a concentration of 1-3 mM of SUC, 2.5 mM of catalyst, respectively). $T_1$=[40±2] s (N=4, pH 3, $B_0$=4.7 T) was significantly prolonged when measured in $D_2O$ (FIG. 15). Preliminary results indicate a further increase in measured $T_1$, to ~50 s, when the hyperpolarized reagent-catalyst mixture was buffered to physiological pH 7 immediately before detection (not shown). The effect of $D_2O$ was found to be a general property of hyperpolarization; for example $T_1$ decay time for HEP was found to be 70 s in $D_2O$ as compared to 50 s in $H_2O$.

Discussion

A reliable, affordable apparatus and methods for hyperpolarization of a biomolecule for routine applications in biomedical research is provided herein. The performance is demonstrated on 1-$^{13}$C-SUCC-d$_{2,3}$, a $^{13}$C PASADENA metabolic agent with the potential to diagnose brain cancer [Chekmenev E. et al., *PASADENA Hyperpolarization of Succinic Acid for MRI and MRS*. Journal of the American Chemical Society 130: (2008) 4212-4213]. This molecule was polarized to an average of $P_{HP}^{t=0}$=[15.3±1.9] in 16 experiments, corresponding to an 49,000 fold enhancement at 4.7 T.

The robust design of the polarizer, reflected in the achieved levels and reproducibility of polarization, qualifies (after reagent-sterility is confirmed) for routine bio-medical/clinical application. Three major factors govern both the reproducibility and level of polarization achieved by PASADENA: (A) The primary source of spin order, parahydrogen (pH$_2$), (B) the hydrogenation of the precursor molecule, and (C) the manipulation of the spins in the hydrogenated molecule to generate a net polarization (by R.F. Spin order transfer sequence, SOT).

(A) The parahydrogen is routinely enriched to >97%, thereby guaranteeing an excellent source of spin order. It proved to be important to allow a minimum of six hours for the cryo-system to cool down, prior to the generation of pH$_2$.

(B) It was noted that an inert atmosphere was a key aspect in the preparation of the PASADENA precursor solution. This is attributed to the sensitivity of the Rhodium (Rh) based catalyst to oxygen and moisture. Therefore, bis(norbornadiene)rhodium (I) tetrafluoroborate should be used fresh and with minimum air and light exposure during the chemical preparation of the catalyst solution. An automated setup under inert atmosphere would be desirable to minimize the exposure of the Rhodium catalyst to atmospheric oxygen, accelerate the preparation process and reduce experimental variability. The duration of the hydrogenation reaction may hold further potential for improvements, as preliminary results indicate. This may be attributed to the progress of the hydrogenation reaction, and the loss of spin order state of molecular and bound parahydrogen while the reaction is going on. However, the hydrogenation reaction was deemed to be complete to >99% within 4 s under 10 bar pH 2 and 62° C., which is supported by the fact that no precursor signal was found in high field NMR spectrum of the hydrogenated sample.

(C) This leaves the spin manipulations by R.F. to explain why the theoretical value of unity, >90%, $^{13}$C polarization was not achieved. The pattern of the spin manipulations tailored to the molecule, and how it is realized by NMR electronics, are essential to achieving hyperpolarization. While the first requires knowledge of the coupling constants of the target molecule, the latter is mostly governed by experimental imperfections of the setup.

The static magnetic field of the 4.7 T MR unit used for the detection of hyperpolarization was found to perturb the relatively low field in the PASADENA polarizer. At a distance of ~7.6±0.1 m, the stray field of the 4.7 T adds a ~0.1 mT horizontal component to the vertical 1.7 mT field of the polarizer. This effect is manifested in a complete loss of hyperpolarization if the polarizer is moved into close proximity of the non-shielded magnet. To avoid thermal drift of the $B_0$ field, a minimum of 4 hours was allowed for the polarizer to reach operational temperature (62° C.).

The sensitivity of the hyperpolarization towards fluctuations in $B_0$ could be reduced by the application of even stronger $B_1$ pulses. However, possible limitations arise: first, large (with respect to $B_0$) $B_1$ fields could make the pulse sequence perform sub-optimally as conventional NMR theory was used for the development (approximation $B_0 \rightarrow B_1$). Second, at strong $B_1$, interaction of $^{13}C$ and $^1H$ has to be taken into account: There is increased cross-talk between the two, and the pulses applied at one Larmor frequency may affect the spins at the other. Moreover, $^2H$ nuclei present in the SUC may be affected by the R.F. pulses as well, a matter not yet investigated in detail. Preliminary simulations suggest that the cross-talk between the two channels can be as large as 9% under the conditions of the present study. These challenges may be significantly alleviated by (1) conducting the hyperpolarization experiment at a higher field (~10 mT) and/or (2) design of shaped pulses for selective excitation at low field.

Conclusion

Methods and apparatus for a semi-automated PASADENA polarizer capable of delivering 2.5-5 ml of highly hyperpolarized biological $^{13}C$ imaging reagents in less than one minute, and capable of repeated delivery every 5-8 minutes, has been achieved and disclosed. The performance of the apparatus is demonstrated on 1-$^{13}C$-SUCC-$d_{2,3}$, an intermediate of the TCA cycle. In 16 experiments, an average polarization of $P_{HP}^{t=0}=[15.3\pm1.9]\%$ was achieved. Tailored transfer sequences make the PASADENA polarizer versatile for a variety of biomolecules, capable of undergoing reaction with parahydrogen necessary for effective PASADENA. Together these descriptions simplify the technology for routine liquid state generation of hyperpolarized molecules for $^{13}C$ and $^{15}N$ subsecond imaging and spectroscopy in vivo and further advance the clinical application of this technology.

While the unique chemical specificity of nuclear magnetic resonance holds great potential in bio-medical research, it is limited by the inherently low polarization (order of $10^{-5}$) to in-vivo detection of major metabolic events (~mM). Routinely available PASADENA hyperpolarization allows the characterization of metabolic events involving less prevalent metabolites in the micro or even nanomolar range.

EXAMPLES

Example 1

The bisphosphine ligand, 1,4-bis-[(phenyl-3-propane sulfonate) phosphine]butane disodium salt was dissolved in $H_2O/D_2O$ to yield 2.5-3.0 mmol/L concentration, followed by removal of oxygen using vacuum and nitrogen connected via a manifold. A rhodium catalytic moiety was then introduced to the reaction mixture under $N_2$ atmosphere as a solution of bis(norbornadiene) rhodium (I) tetrafluoroborate in acetone with 5% molar excess of bisphosphine ligand with respect to rhodium. The resulting solution was vigorously shaken and acetone was removed under vacuum (Solution B). For demonstration of hyperpolarization, a readily available, but toxic PASADENA reagent, hydroxyethyl acrylate 1-$^{13}C$ (99%), 2,3-d (98%), ("HEA"), was prepared as an aqueous solution, 2-5 mg HEA and dissolved in a small volume of phosphate buffer, pH 7.0, mixed with the catalyst solution and de-aerated by application of a vacuum through a Schlenk line (Solution A). The completed PASADENA solution of precursor and catalyst was drawn into a 20 mL plastic syringe and connected to valve 2 of the PASADENA polarizer (FIG. 5), to allow the injection of a desired amount of imaging reagent for each experiment. When prepared in these proportions, hydrogenation of the precursor was carried to completion until no residual precursor (HEA) could be detected by $^{13}C$ NMR.

Example 2

Quantification and Reproducibility of Polarization

Figure 16:
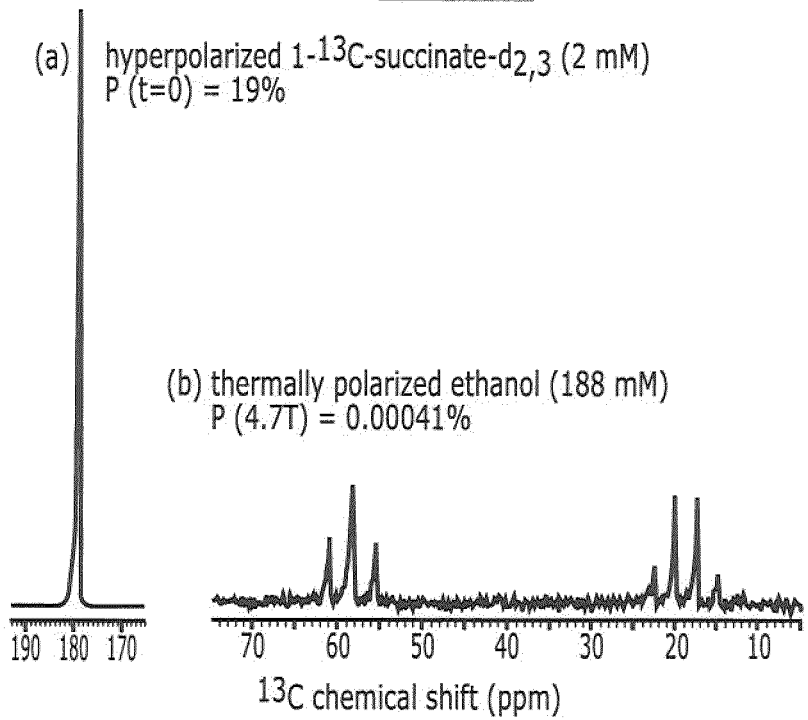
FIG. 16. A graph of the quantification of polarization.

Repeated hyperpolarization experiments of 1-$^{13}C$-SUCC-$d_{2,3}$ in $D_2O$ were carried out to determine the level and stability of the polarization produced by the PASADENA polarizer. A representative $^{13}C$ spectrum of hyperpolarized $^{13}C$-SUCC-$d_{2,3}$ is demonstrated in FIG. 16a. Peak amplitude was quantified by comparison with the spectrum of ethanol (FIG. 16b), using the equations described herein.

Polarization of $^{13}C$ succinate in $D_2O$ achieved 19%, corresponding to an overall enhancement of 47,000 fold at 4.7 Tesla. To define the reproducibility of polarization, 28 further studies were performed. Note that since each experiment takes only 2-3 minutes, with allowance for rinsing and reloading of the polarizer, the automated polarizer permitted as many as 10 PASADENA hyperpolarizations each hour. Studies in $H_2O$ (N=12) (not shown) and in $D_2O$ (N=16) (Table 8) were performed. Hyperpolarization $P_{HP}^{t=0}=[15.3\pm1.9]\%$ was reproducibly achieved in 16 hyperpolarization experiments on 1-$^{13}C$-SUCC-$d_{2,3}$, in $H_2O$ before the B1 calibration had been completed (Table 8).

Greater reproducibility and higher absolute polarization were achieved after B1 calibration and when the procedure was performed in $D_2O$ (Table 8). Detailed results are presented graphically in FIG. 17. The average polarization achieved in $D_2O$, calculated from T1 to be that at the point of production, was $P_{HP}^{t=0}=[12.8\pm3.1\%]$ on 1-$^{13}C$-SUCC-$d_{2,3}$ (2-5 mM) for 16 experiments in four series. The intra day variability was found to be (1) $P_{HP}^{t=0}=[16.5\pm3.3]\%$, N=3, (2) $P_{HP}^{t=0}=[15.9\pm2.0]\%$, N=4, (3) $P_{HP}^{t=0}=[14.8\pm0.1.3]\%$, N=5, (4) $P_{HP}^{t=0}=[15.9\pm0.2.0]\%$. This corresponds to a relative enhancement of $\eta^{t=0}=37,400\pm4,600$ at 4.7 T. More relevant to the conduct of experiments was the degree of hyperpolarization at the point of measurement. As expected with a mean delay of 33 seconds for delivery and T1=27 to 40 seconds, enhancement was significantly lower=5.4±1.3% in water and 6.4±0.8% in D20 (enhancement ~37,4000×[6.5/15.3]=15, 900 fold at the point of measurement).

No effect of the concentration of $^{13}C$-SUCC-$d_{2,3}$ on the level of hyperpolarization was found over a narrow range of concentrations 1.65-2.89 mM (in water) or from 0.96-2.93 mM (in $D_2O$; Table 8).

Example 3

Efficacy of Hyperpolarized 1-$^{13}C$ Succinate In Vivo

Figure 18:
FIG. 18. An in vivo $^{13}C$ image of rat achieved after close-arterial injection of 1 mL of hyperpolarized $^{13}C$ succinate.

FIG. 18 demonstrates, in a representative $^{13}C$ image, overlaid on a standard proton image, the efficiency of hyperpolarized reagent for in vivo imaging. After rapid ante-grade injection into the common carotid artery, hyperpolarized $^{13}C$ succinate appeared in the anatomical distribution coincident with the rat brain, as outlined by $^1H$ MRI.

Example 4

Figure 20A:
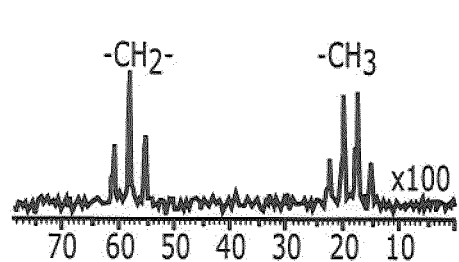
FIG. 20a. Graph of $^{13}C$ reference spectrum of 2.8 mL 17 M ethanol with 188 mM $^{13}C$ concentration per site.
Figure 20B:
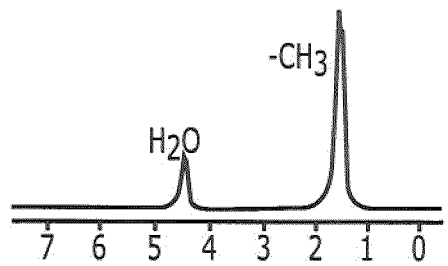
FIG. 20b. Graph of $^1H$ NMR spectrum of 2.8 mL 3M sodium $^{13}C$-acetate in $D_2O$.
Figure 20C:
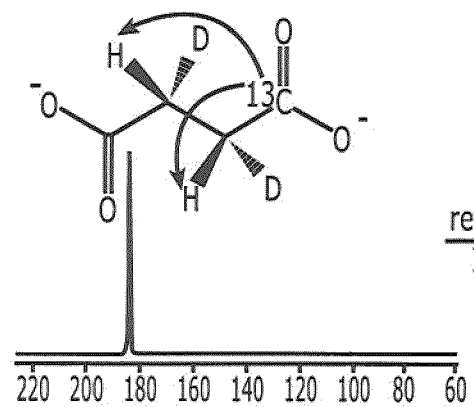
FIG. 20c. Graph of $^{13}C$ NMR spectrum of hyperpolarized 6.2 mM 1-$^{13}C$-succinate-$d_{2,3}$, $^{13}C$ polarization of 5.5% after being stored for 70 s, $T_1$=105 s, the spectrum is acquired using a 12° excitation pulse.
Figure 20D:
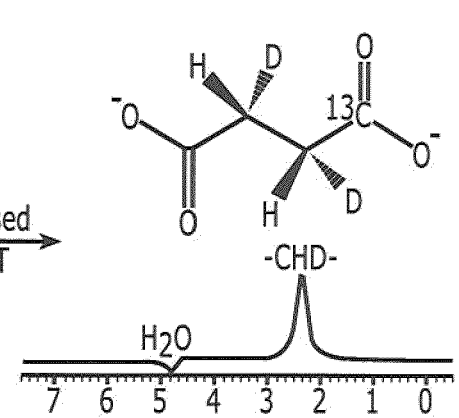
FIG. 20d. Graph of $^1H$ NMR spectrum of hyperpolarized 6.2 mM 1-$^{13}C$-succinate-$d_{2,3}$ where net $^1H$ signal enhancement is 1,350 fold with 41% spin polarization transfer efficiency.
Figure 20E:
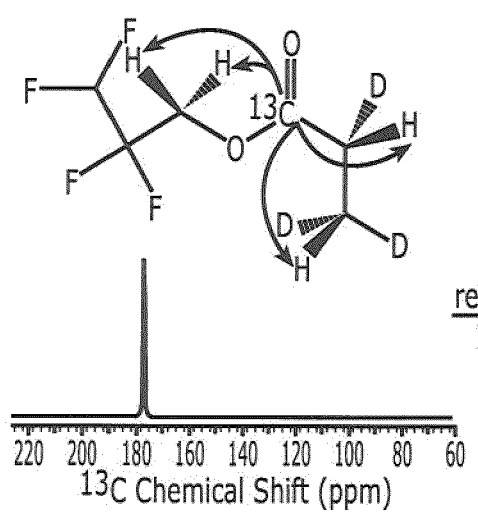
FIG. 20e. Graph of $^{13}C$ NMR spectrum of hyperpolarized 2.9 mM TFPP. $^{13}C$ polarization is 9.5% after being stored for 24 s, $T_1$=67 s. The spectrum is acquired using a 12° excitation pulse, FIG. 20f. Graph of $^1H$ NMR spectrum of hyperpolarized 2.9 mM TFPP where net $^1H$ signal enhancement is 2,930 fold with 51% efficiency.
Figure 20F:
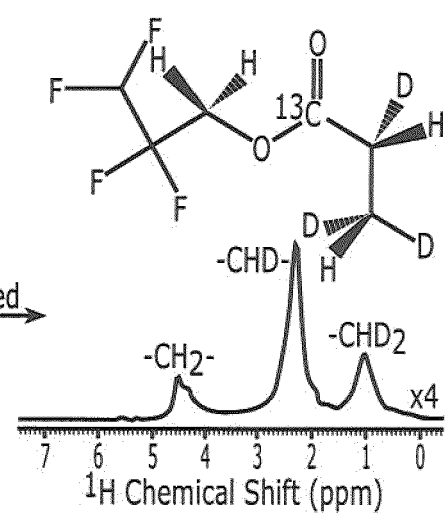

Sensitivity Improvement of $^{15}N$ and $^{13}C$ Hyperpolarized Molecular Agents A sample containing 2.4 mL of 6.2 mM 1-$^{13}C$-succinate-$d_2$ was hyperpolarized at the $^{13}C$ site to 10.7%. Hyperpolarization was then kept on $^{13}C$ for 70 s. During this time, the polarized sample was transferred from a low magnetic field polarizer operating at 1.76 mT to 4.7 T animal MR scanner. The $^{13}C$ polarization decayed from 10.7% to 5.5% corresponding to final $^{13}C$ signal enhancement by a factor of 13.500. Then the refocused INEPT pulse sequence[10] with $\tau_{INEPT}$=34 ms and $\tau_{refocus}$=32 ms (FIG. 19) was used to transfer polarization from $^{13}C$ to protons within 1-$^{13}C$-succinate-$d_2$ (FIG. 20a and FIG. 20b). The results indicated that the two protons were successfully hyperpolarized corresponding to 41% polarization transfer efficiency and 1,350 fold $^1H$ NMR signal enhancement per two methylene protons. In a follow up experiment, 2.4 mL of 2.9 mM TFPP was polarized to 14% and the hyperpolarization was stored on the 1-$^{13}C$ site for 24 s, during which the polarization decayed to 9.5% corresponding to the final signal enhancement of 23,300 fold at this site (FIG. 20e). The delays of the refocused INEPT were $\tau_{INEPT}$=20 ms and $\tau_{refocus}$=16 ms. The combined intensity of the three NMR lines corresponding to four hydrogen atoms (FIG. 20f) was enhanced by a factor of 2,930, corresponding to the 50% polarization transfer efficiency by the refocused INEPT sequence.

Example 5

Computer Software

A custom programs based on the LabView platform was developed. The main features included the control of the digital outputs for mechanized mixing, delivery and recovery of imaging products in the correct sequence and application of a R.F. sequence with precise timing. The R.F. sequence for each experiment was saved in a separate file and reloaded to the program in the form of an ACSII file as necessary.

Various embodiments of the subject matter are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

While particular embodiments of the present subject matter have been shown and described, it will be obvious to those skilled in the art that, based upon the teachings herein, changes and modifications may be made without departing from this subject matter and its broader aspects and, therefore, the appended claims are to encompass within their scope all such changes and modifications as are within the true spirit and scope of this subject matter. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.

TABLE 1

Fluid Control Unit

| Function | Part | Description | Commercial availability |
|---|---|---|---|
| Transport and reaction | Tubing | PTFA tubing | Y[1] |
| | Valves | Electromagnetic solenoid and manual valves | Y[2, 3, 4] |
| | Ante+-chamber | PTFA tubing | Y[1] |
| | Reaction chamber | Injection cap, reactor body, end cap | — |
| Aux | T control | Heater, fan, controller, relay | Y[5] |
| | Injection timer | On-delay relay | Y[6] |
| | Intake precursor | 30 ml rubber piston syringe | Y[7] |

TABLE 2

Low Field NMR Unit

| Function | Part | Description | Commercial availability |
|---|---|---|---|
| B1 field | B1 coil | Saddle-shaped coil | — |
| | Synthesizer | DAC analog-out | Y[8] |
| | Amplifier | Audio amplifier | Y[9] |
| | Filter | 150 kHz low-pass filter | Y[10] |
| | Monitoring | Oscilloscope | Y[11] |
| | Cables | Coaxial cable RG58 | Y[12] |
| Bo field | Bo coil | Solenoid coil | — |
| | Power supply | DC power supply | Y[13] |
| | Monitoring | Gauss meter | Y[14] |

TABLE 3

Process Control Unit

| Function | Part | Description | Commercial availability |
|---|---|---|---|
| Software | Platform | LabView | Y[15] |
| | Program | pPASADENA control V1.1 | — |
| Hardware | Synthesizer | DAC analog-out | Y[8] |
| | Valve, trigger control | DAC digital-out | Y[16] |
| | | Relays | Y[17] |

TABLE 4

Parahydrogen Generator

| Function | Description | Commercial availability |
|---|---|---|
| Low T Unit | Helium two stage cold head | Y[18] |
| | Pressure gauge | Y[19] |
| | Vacuum shroud | Y[20] |
| | Helium compressor/cryodrive | Y[23] |
| | Vacuum pump | Y[24] |
| | Valve | Y[25] |
| | Flow limiter | Y[26] |
| | Relay | Y[27] |
| | Pressure display | Y[28] |
| | Water cooler | Y[29] |
| | Tubing connectors | Y[30] |
| | Regulator for $H_2$ supply | Y[31] |
| | Tubing at ambient T | Y[32] |
| | Flow meter | Y[33] |
| Catalytic converter | Low T conversion container | Y[34] |
| | Catalyst | Y[35] |
| Storage | Cylinder | Y[36] |

TABLE 5

Chemicals and Axillaries

| Function | Part | Description | Commercial availability |
|---|---|---|---|
| Chemicals | Precursor | 1-$^{13}$C FUM-d2,3, 1-$^{13}$C HEA-d2,3 | Y[37, 38] |
| | Catalyst | Rh-complex and ligand | Y[39, 40] |
| | Solvent | D$_2$O, H$_2$O, buffer | Y[41] |
| Aux Lab Equipment | | Schlenk line with vacuum, N$_2$, in fume hood | Y[41] |
| | | Glass ware | Y[41] |
| | | Precision scale | Y[41] |

TABLE 6

Workflow of the PASADENA experiment. Automated software controls the time sensitive steps.

| (a) Event Nr. | (b) Time point | (c) Description | (d) Duration |
|---|---|---|---|
| *Manual preparation/Manual control* | | | |
| *Clean polarizer:* | | | |
| 1 | 0 s | Flush lines and reactor with 14 b N2 gas (Valve V2, V3, V4, V5). Preheat precursor solution: | 10 s |
| 2 | 10 s | Transfer 3.5 mL of precursor into the injection line (V2). | 120 s |
| Total time for preparations: 130 s | | | |
| *Automated procedure/computer control/Automated sequence* | | | |
| 1 | 0 s | Fill reaction chamber with pH 2 (V1). Hydrogenation reaction: | 10 s |
| 2 | 10 s | Inject the precursor into the reactor (V3, V4). Apply R.F. 1H decoupling sequence. Hyperpolarization: | 3 s |
| 3 | 13 s | Apply R.F. spin order transfer sequence. | >1 s |
| 4 | 14 s | Expel hyperpolarized agent (V5). | 2 s |
| 5 | 19 s | Delivery agent and rest (V5). Signal detection: | 28 s |
| 5 | 52 s | Send trigger signal | 3 s |
| Total time for hyperpolarization: 52 s | | | |

TABLE 7

Protocol for PASADENA hyperpolarization.

| A. Prerequisites | B. Setup/Installation | C. Experimental routines |
|---|---|---|
| 1. Parahydrogen (>95%) | Setup of polarizer: 1. Fluid control system; | 1. Flush the polarizer |
| 2. Precursor molecule(s) | 2. Low field NMR system | 2. Flush delivery system |
| 3. Hydrogenation catalyst | Calibrate low field NMR system: | 3. Prepare 4.7T MRI scanner |
| 4. PASADENA Polarizer | 3. Center frequency $^1$H, $^{13}$C | 4. Check temperature |
| | 4. Flip angles $^{13}$C, $^1$H | 5. Check gas pressure (N$_2$, pH$_2$) |
| | 5. J couplings for target molecule | 6. Check B$_0$ value |
| | Optimize Spin order transfer: 6. B$_0$ optimization | 7. Check R.F. amplitudes of B$_1$ pulses |
| | 7. B$_1$ optimization | |

Summary of the minimum requirements for successful hyperpolarization using prototype polarizer. A systematic description of PASADENA methodology follows. Tasks required to establish PASADENA hyperpolarization, optimize the operating equipment and provide quality assurance in daily use are summarized under these headings.

TABLE 8

Reproducibility and performance of the polarizer:

| | (A) Number | (B) $P_{HP}^{t=0}$ (%) | (C) $P_{HP}^{t=33\,s}$ (%) | (D) c (SUCC) (mM) | (E) c (Rh) (mM) |
|---|---|---|---|---|---|
| Day 1 | 1 | 15.5 | 6.5 | 1.71 | 2.2 |
| | 2 | 20.1 | 8.4 | 1.71 | 2.2 |
| | 3 | 13.8 | 5.8 | 1.71 | 2.2 |
| Day 1, N = 3: | $P_{HP}^{t=0} = [16.5 \pm 3.3]\%$ $P_{HP}^{t=33\,s} [6.9 \pm 1.3]\%$ | | | | |
| | 4 | 17.1 | 7.2 | 1.4 | 2.2 |
| | 5 | 15.9 | 6.7 | 1.4 | 2.2 |
| | 6 | 17.5 | 7.3 | 1.4 | 2.2 |
| | 7 | 13.0 | 5.5 | 0.96 | 2.2 |
| Day 2, N = 4: | $P_{HP}^{t=0} = [15.9 \pm .2.0]\%$ $P_{HP}^{t=33\,s} = [7.1 \pm 0.3]\%$ | | | | |
| | 8 | 14.9 | 6.2 | 2.93 | 2.1 |
| | 9 | 15.4 | 6.4 | 2.93 | 2.1 |
| | 10 | 16.3 | 6.8 | 1.24 | 2.2 |
| | 11 | 14.7 | 6.2 | 1.24 | 2.2 |
| | 12 | 12.7 | 5.3 | 1.24 | 2.2 |
| Day 3, N = 5: | $P_{HP}^{t=0} = [14.8 \pm .1.3]\%$ $P_{HP}^{t=33\,s} = [6.5 \pm 0.3]\%$ | | | | |
| | 13 | 15.3 | 6.4 | 1.59 | 2.2 |
| | 14 | 14.3 | 6.0 | 1.95 | 2.2 |
| | 15 | 15.1 | 6.3 | 1.59 | 2.2 |
| | 16 | 13.3 | 5.6 | 2.07 | 2.2 |
| Day 4, N = 4: | $P_{HP}^{t=0} = [14.5 \pm 0.9]\%$ $P_{HP}^{t=33\,s} = [6.2 \pm 0.2]\%$ | | | | |
| Total N = 16 | $P_{HP}^{t=0} = [15.3 \pm 1.9]\%$ $P_{HP}^{t=33\,s} = [6.4 \pm 0.8]\%$ | | | | |

Figure 17:
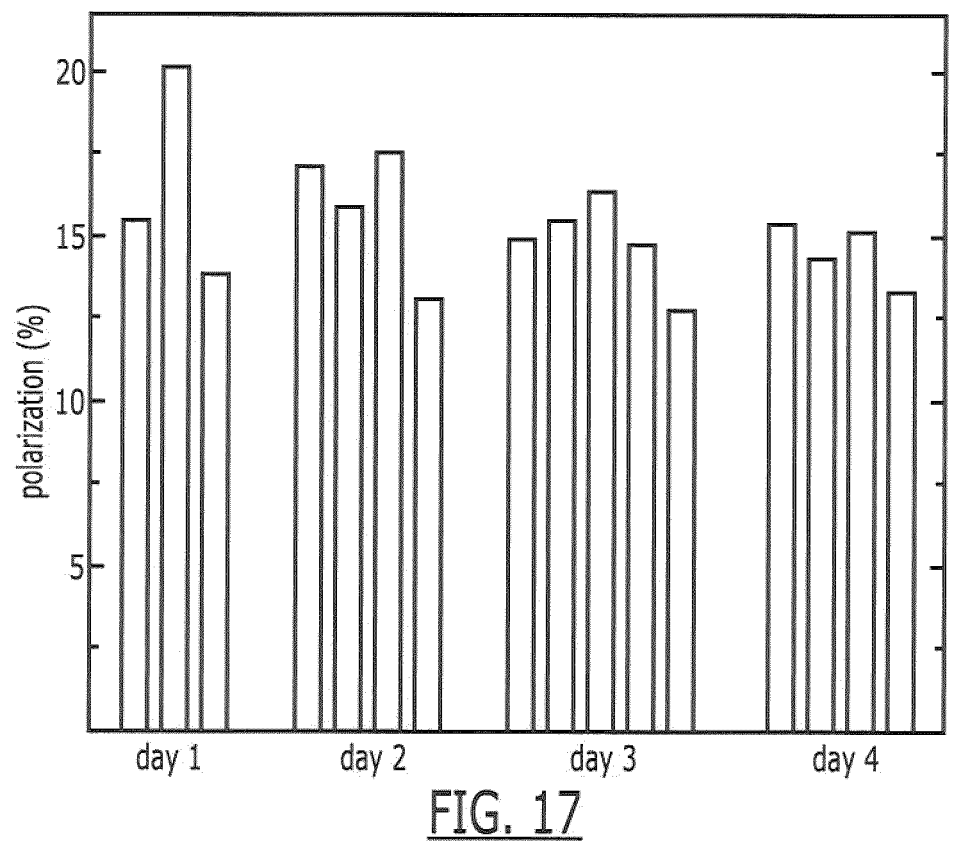
FIG. 17. A graph of the data collected for reproducibility of hyperpolarization.

(A) Number of experiment
(B) Level of nascent polarization (T$_1$ = 40 s)
(C) Level of polarization after 33 s
(D) Concentration of 1-$^{13}$C—SUCC-d$_{2,3}$ in mM
(E) Concentration of Rh-catalyst complex in mM Four different sets of experiments of hyperpolarization of 1-$^{13}$C-SUCC-d$_{2,3}$, in D$_2$O were performed as indicated (see also FIG. 17).

TABLE 9

Source of Materials

1. PTFA tubing, OD/ID/WT: ⅛, 1/16, 1/32, Nalgene, NY, USA
2. Two-ways rocker valve, mod. 6126 (id. 431568, for liquids), Burkert Fluid Control Systems, Indelfingen, Germany
3. Addition to 6126 by Promech, Malmö, Sweden
4. Solenoid valve, mod. H22G9DGV (for gases), Peter Paul Co., CN, USA
5. Mod. CN132, Omega Engineering, CN, USA
6. Mod. 814 Syrelec, Crouzet, TX, USA
7. BD, Franklin Lanes, NJ, 07417, USA
8. Mod. PXI 1042, PXI 8331, PXI 6251, National Instruments, TX, USA
9. Mod. 8522 TX, Onkyo, USA
10. Mod. 3200, Krohn Hite, USA
11. Mod. TDS 3012 B 100 MHz 1.25 Gs/s, Tectronix, USA
12. Generic
13. Mod. 3615A, Agilent, USA
14. Gaussmeter 450 with axial probe MMA 2508 VH, Lake shore, USA
15. LabView (V. 8), National Instruments, TX, USA
16. Mod. USB 6501, NI, TX, USA
17. Mod. ER-16, NI, TX, USA
18. Mod. B51907000 6130 cold head assembly, Edwards, MA, USA
19. Active pirani gauge, APG M NW 25 ST/ST, PN: D0217200 SN: 02723484
20. Generic, S.C.B., Herrmann-Cossmann-Str. 19, D-41472 Neuss, Germany
23. 3.0 kW He cryodrive, Edwards, MA, USA
24. Mod. RV3, with oil mist filter EMF 10, Edwards, MA, USA
25. Mod. LCPV2 5 EKA, Edwards, MA, USA
26. Needle valve HAKE 1315G4s 5000 PSI 1345 b 1 0553, set 4.5
27. generic, 240 V
28. Mod. AGD, set to ~2 × $10^{-4}$ b, Edwards, MA, USA
29. Mod. Neslab Merlin M150, Thermo Fischer Scientific, MA, USA
30. "Instrumentation-quick-connect" (SS), Swagelok, OH, USA
31. Regulator 250 b to 68 b. Advanced specialty gas equipment, NJ, USA
32. ¼" copper/¼" SS generic, 7RSW SAE 100 R7-4¼ 2750 PSI swagelok, OH, USA
33. Mod. 7101 043001A, King Instruments, CA, USA
34. ¼" copper tubing, generic
35. Ionex-Type O-P catalyst (hydrous ferric oxide), Molecular products, CO, USA
36. 7 L volume, M25x2 150, CBM produkter AB, Box 47, 131 06 Nacka, Sweden, or P2795z, Luxfer, CA, USA
37. fumaric acid, 1-$^{13}$C (99%), 2, 3 -$d_2$ (96%), Cambridge Isotope Laboratories, MA, USA
38. hydroxyethyl acrylate 1-$^{13}$C (99%), 2, 3, 3, -$d_3$ (98%), Isotech, Sigma-Aldrich, MO, USA
39. bis(norbornadiene)rhodium(I) tetrafluroborate, catalog number 45-0230, CAS 36620-11-8, >96%, Strem Chemicals, MA, USA
40. 1,4-bis[(phenyl-3-propanesulfonate)phosphine] butane disodium salt, Q36333, Isotech, Sigma Aldrich, MO, USA.
41. generic

What is claimed is:

1. An apparatus for hyperpolarization, comprising:
a reaction chamber for hyperpolarization;
a transmitter device for transmission of radio frequency (R.F.) pulses into the reaction chamber;
a static magnetic field generator for generating a static magnetic field surrounding the reaction chamber; and
a plurality of valves employed for fluid and/or gas flow and delivery to and from the reaction chamber;
wherein an image reagent solution is introduced, via one of the valves in the plurality, into and hyperpolarized within the reaction chamber.

2. The apparatus of claim 1, further comprising:
a power source for supplying power to the transmitter device and the static magnetic field generator.

3. The apparatus of claim 1, further comprising:
a central processor, wherein the central processor controls said plurality of valves employed for fluid flow and delivery of an image reagent solution to and from the reaction chamber for hyperpolarization.

4. The apparatus of claim 1, further comprising an image reagent solution source in communication with the reaction chamber for supplying the image reagent solution.

5. The apparatus of claim 1, further comprising a parahydrogen generator in communication with the reaction chamber for generating and delivering parahydrogen.

6. The apparatus of claim 1, further comprising a nitrogen source in communication with the reaction chamber for supplying nitrogen.

7. The apparatus of claim 2, further comprising a Hall sensor for monitoring the strength and stability of the power source.

8. The apparatus of claim 7, wherein the Hall sensor is located between the transmitter device and the reaction chamber.

9. The apparatus of claim 1, wherein each valve in the plurality is composed of a material independently selected from a group consisting of polytetrafluoroethylene, perfluoroalkoxy polymer resin, fluorinated ethylene-propylene, fluoropolymer, fluorocarbon, polysulfone, and combinations thereof.

10. The apparatus of claim 1, wherein the valves in the plurality are electromagnetic solenoid valves, pinch valves, or combinations thereof.

11. The apparatus of claim 1, wherein application of the transmitter device and static magnetic field generator in conjunction with the handling of the image reagent solution is controlled by a central processor.

12. The apparatus of claim 1, further comprising a synthesizer in communication with the transmitter device for facilitating radio frequency pulse transmission.

* * * * *